US009075014B2

(12) United States Patent
Sames et al.

(10) Patent No.: US 9,075,014 B2
(45) Date of Patent: Jul. 7, 2015

(54) PH-RESPONSIVE FLUORESCENT FALSE NEUROTRANSMITTERS AND THEIR USE

(75) Inventors: Dalibor Sames, New York, NY (US); David Sulzer, New York, NY (US); Minhee Lee, Bellevue, WA (US); Niko Gubernator, Del Mar, CA (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 13/575,535

(22) PCT Filed: Jan. 28, 2011

(86) PCT No.: PCT/US2011/022951
§ 371 (c)(1),
(2), (4) Date: Mar. 20, 2013

(87) PCT Pub. No.: WO2011/094560
PCT Pub. Date: Aug. 4, 2011

(65) Prior Publication Data
US 2013/0171664 A1 Jul. 4, 2013

(51) Int. Cl.
*C07D 311/00* (2006.01)
*G01N 21/64* (2006.01)
*C07D 311/16* (2006.01)

(52) U.S. Cl.
CPC .......... *G01N 21/6486* (2013.01); *C07D 311/16* (2013.01)

(58) Field of Classification Search
CPC ...................................... C07D 311/08
USPC ...................................... 546/289
See application file for complete search history.

(56) References Cited

U.S. PATENT DOCUMENTS

| | | | |
|---|---|---|---|
| 2,334,348 | A | 11/1943 | Miglarese |
| 3,352,885 | A | 11/1967 | Schellhammer et al. |
| 3,899,529 | A | 8/1975 | Witzel et al. |
| 5,989,535 | A | 11/1999 | Nayak |
| 2004/0058983 | A1 | 3/2004 | Vuorela et al. |
| 2005/0170442 | A1 | 8/2005 | Kupcho et al. |
| 2008/0194522 | A1 | 8/2008 | Chen et al. |
| 2009/0005436 | A1 | 1/2009 | Carotti et al. |
| 2009/0267026 | A1 | 10/2009 | Goto et al. |
| 2010/0035279 | A1 | 2/2010 | Gubernator et al. |
| 2010/0048604 | A1 | 2/2010 | Yee et al. |
| 2013/0190497 | A1 | 7/2013 | Gubernator et al. |

FOREIGN PATENT DOCUMENTS

| | | | | |
|---|---|---|---|---|
| EP | WO 2006102958 | * | 10/2006 | ........... C07D 311/08 |
| JP | 02-043521 | | 2/1990 | |
| JP | WO 9315219 | * | 8/1993 | ............... C12Q 1/28 |
| JP | 05-263072 | | 10/1993 | |
| WO | WO 2006/023821 | | 3/2006 | |
| WO | WO 2006/026368 | | 3/2006 | |
| WO | WO 2006/102958 | | 10/2006 | |
| WO | WO 2007/022263 | | 2/2007 | |
| WO | WO 2008/013997 A2 | | 1/2008 | |
| WO | WO 2011/094560 | | 8/2011 | |
| WO | WO 2013/028999 | | 2/2013 | |

OTHER PUBLICATIONS

Partilla et al. (2006). Interaction of amphetamines and related compounds at the vesicular monoamine transporter. *The Journal of Pharmacology and Experimental Therapeutics*, 319(1), 237-246.
Notification of Transmittal of the International Search Report and the Written Opinion of the International Searching Authority, or the Declaration, including an International Search Report and Written Opinion of the International Searching Authority, mailed May 4, 2011 in connection with PCT International Application No. PCT/US2011/022951, filed Jan. 28, 2011.
International Search Report in connection with PCT/US2005/30276 issued Jun. 20, 2006.
International Preliminary Report on Patentability in connection with PCT/US2005/30276 issued Feb. 28, 2007.
Written Opinion issued Jun. 20, 2006 in connection with PCT/US2005/30276.
Notification of Transmittal of the International Search Report and the Written Opinion of the International Searching Authority, of the Declaration in connection with PCT/US05/29722 issued Jul. 25, 2008.
International Search Report in connection with PCT/US05/29722 issued Jul. 25, 2008.
Written Opinion issued Jul. 25, 2008 in connection with PCT/US05/29722.
Notification Concerning Transmittal of International Preliminary Report on Patentablity in connection with PCT/US2005/029722 issued Mar. 5, 2009.
International Search Report in connection with PCT/US2006/031979 issued Jan. 8, 2007.

(Continued)

*Primary Examiner* — Nizal Chandrakumar
(74) *Attorney, Agent, or Firm* — John P. White; Cooper & Dunham LLP

(57) ABSTRACT

This invention relates to compounds having the following structure:

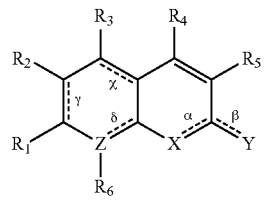

wherein Y is O, X is O, bond α is absent and bond β is present, or Y is H, X is CH, bond α is present, and bond β is absent; atom Z is a carbon and bonds χ, δ and γ are present, or atom Z is a nitrogen and bonds χ, δ and γ are absent, or atom Z is a nitrogen and bonds χ and δ are present and γ is absent. $R_1$, $R_2$, $R_3$, $R_4$, $R_5$, and $R_6$ are various substituents as described in the specification.

14 Claims, 13 Drawing Sheets

(56) References Cited

OTHER PUBLICATIONS

International Preliminary Report on Patentability in connection with PCT/US2006/031979 issued Feb. 20, 2008.
Written Opinion issued Jan. 8, 2007 in connection with PCT/US2006/031979.
International Search Report in connection with PCT/US2007/017014 issued Sep. 19, 2008.
Written Opinion in connection with PCT/US2007/017014 issued Sep. 19, 2008.
Notification Concerning Transmittal of International Preliminary Report on Patentablity in connection with PCT/US2007/017014 issued Feb. 5, 2009.
Written Opinion of the International Search Authority issued May 4, 2011 in connection with International Application PCT/US2011/022951.
International Search Report issued May 4, 2011 in connection with International Application PCT/US2011/022951.
Notification of Transmittal of International Preliminary Report on Patentability Chapter I and International Preliminary Report on Patentability Chapter I issued Jul. 31, 2012 in connection with International Application PCT/US2011/022951.
Extended European Search Report issued May 24, 2013 in connection with European Patent Application EP20110737741.
Office Action issued Apr. 5, 2011 in connection with U.S. Appl. No. 11/661,152.
Final Office Action issued Oct. 18, 2011 in connection with U.S. Appl. No. 11/661,152.
Advisory Action issued Feb. 24, 2012 in connection with U.S. Appl. No. 11/661,152.
Office Action Issued Sep. 15, 2011 in connection with U.S. Appl. No. 12/309,724.
Final Office Action Issued Apr. 30, 2012 in connection with U.S. Appl. No. 12/309,724.
Advisory Action Issued Jul. 6, 2012 in connection with U.S. Appl. No. 12/309,724.
Notice of Allowance Issued Aug. 20, 2012 in connection with U.S. Appl. No. 12/309,724.
CAS Online, Document No. 48:14743, Reg. No. 14415-44-2 (1954).
CAS Online, Document No. 115:182261, Reg. No. 136449-44-0 (1991).
CAS Online, Document No. 118:52524, Reg. No. 14415-44-2 (1993).
CAS Online, Document No. 69:93083 (1968).
Chen et al. (2005) "Design of Optical Switches as Metabolic Indicators: Fluorogenic Probes for Monoamine Oxidases (MAO A and MAO B)" J. Am. Chem. Soc. vol. 127, 4544-4545.
Edenharder et al. (1997) "Inhibition of the Mutagenicity of 2-Nitrofluorene, 3-Nitrofluoranthene and 1-Nitropyrene by Flavonoids, Coumarins, Quinones and Other Phenolic Compounds" Food and Chemical Toxicology, vol. 35, 357-372.
Gubernator et al. (2009) "Fluorescent False Neurotransmitters Visualize Dopamine Release from Individual Presynaptic Terminals" Science 2009 vol. 324, 1441-1444.
Lee et al. (2010) "Development of pH-Responsive Fluorescent False Neurotransmitters." J. Am. Chem. Soc., vol. 132, 8828-8830.
Nitz, M. (2002) Enantioselective synthesis and application of the highly fluorescent and environment-sensitive amino acid 6-(2-diemthylaminonaphthoyl)alanine (DANA). Chem Commun, Issue 17, pp. 1912-1913.
Raj et al. (1998) "Mechanism of Biochemical Action of Substituted 4-Methylbenzopyran-2-ones. Part I: Dioxygenated 4-Methyl Coumarins as Superb Antioxidant and Radical Scavenging Agents" Bioorganic & Medicinal Chemistry, vol. 6, p. 833-839.
Pisani, L. et al. (2009) "Discovery of a Novel Class of Potent Coumarin Monoamine Oxidase B Inhibitors: Development and Biopharmacological Profiling of 7-[(3-Chlorobenzyl)oxy]-4-[(methylamino)methyl]-2H-chromen-2-one Methanesulfonate (NW-1772) as a Highly Potent, Selective, Reversible, and Orally Active Monoamine Oxidase B Inhibitor" J. Med. Chem., vol. 52, 6685-6706.
Prabhakar Rao B.V.V.S.N. et al. (1997) "Theoretical study on naphthyl-phenylacetylenes for second-order nonlinear optical applications." Can. J. Chem., vol. 75, pp. 1041-1046.
Sundt, T. et al. (1978) "Brain pH Measurments Using a Diffusible, Lipid Soluble pH Sensitive Fluorescent Indicator" J. of Neurochemistry., vol. 31. 627-635.
Yee, D.J. et al. (2004) "New tools for molecular imaging of redox metabolism: Development of a fluorogenic probe fpr 3-alpha-hydroxysteroid dehydrogenases." J. Am. Chem. Soc., vol. 126, pp. 2282-2283.
Zhou, X. (2002) "Synthesis and NKT Cell Stimulating Properties of Fluorophore- and Biotin-Appended 6"-amino-6"deoxy-galactosylceramides." Org. Lett., vol. 4, No. 8, pp. 1267-1270.
Office Action Issued Oct. 25, 2013 in connection with U.S. Appl. No. 13/718,832.
Office Action Issued May 20, 2014 in connection with U.S. Appl. No. 13/718,832.
Office Action Issued Mar. 13, 2014 in connection with U.S. Appl. No. 11/661,152.

\* cited by examiner

PH-RESPONSIVE FLUORESCENT FALSE NEUROTRANSMITTERS AND THEIR USE

This application is a §371 national stage of PCT International Application No. PCT/US2011/022951, filed Jan. 28, 2011, claiming the benefit of U.S. Provisional Application No. 61/337,018, filed Jan. 29, 2010, the contents of each of which are hereby incorporated by reference in their entirety.

Throughout this application, certain publications are referenced in brackets. Full citations for these publications may be found immediately preceding the claims. The disclosures of these publications in their entireties are hereby incorporated by reference into this application in order to describe more fully the state of the art to which this invention relates.

BACKGROUND OF THE INVENTION

There is an interest in visualization of neurotransmission for optical imaging of metabolic and signaling enzymes in cells and tissues. [1, 2]

Dopaminergic neurotransmission plays key roles in motivational behavior, reward and habit learning, working memory and cognition, while aberrations in presynaptic dopamine stores and release underlie important aspects of psychiatric disorders including schizophrenic and amphetamine-triggered psychosis, ADHD and drug addiction as well as Parkinson's disease and methamphetamine toxicity.

The termination of neurotransmitter action is determined by a number of factors, including their reuptake into nerve terminals by monoamine transporters, their dilution by diffusion out of the synaptic cleft, and their metabolism by Monoamine Oxidase. Specific monoamine transporters located in the neuronal plasma membrane terminate the action of neurotransmitters by transporting them back into presynaptic terminals. Once inside the presynaptic terminal, vesicular monoamine transporters mediate their filling into secretory vesicles. All characterized monoaminergic cells utilize the vesicular monoamine transporter (VMAT) to accumulate monoamines from the cytoplasm into vesicles. These VMATs are polytopic membrane proteins, which act as electrogenic antiporters (exchangers) of protons and monoamines utilizing an acidic and positively polarized granule matrix.

The monoamine transporters of synapses formed by the midbrain dopamine projections are involved in voluntary motor control, reward and learning, and are the primary target of drugs of abuse including amphetamine, nicotine, cocaine as well as therapeutic agents that are used to treat mood disorders. Neuronal death in the substantia nigra is the cause of Alzheimer's disease and a decreased density of dopamine monoamine transporter has been found in Parkinson's, Wilson's, and Lesch-Nyhan's disease, while a decrease in serotonin monoamine transporter level is found in patients suffering from major depression and aggressive behavior.

Fluorescent false neurotransmitters (FFNs), probes that act as optical tracers of dopamine and provide the first means to image neurotransmitter release from individual presynaptic terminals in the brain have recently been introduced. [3] FFNs have been designed to act as tracers of dopamine to enable direct visualization of neurotransmitter uptake and release at individual synaptic terminals. FFNs represent a novel class of imaging probes that are small organic compounds that fulfill the following criteria: (a) like dopamine, they accumulate into synaptic vesicles and chromaffin vesicles in a manner dependent on the vesicular monoamine transporter (VMAT) and pH gradient; (b) like dopamine, they are released with vesicle fusion; (c) unlike dopamine, they are intensely fluorescent so that they can be used in low concentrations to avoid interference with normal transmitter release; (d) they are non-toxic and photostable, limiting bleaching. FFNs are described in PCT/US2007/017014 (WO 2008/013997), which is hereby incorporated by reference in its entirety.

A non-fluorescence-based technology, Positron Emission Tomography (PET), enables CNS imaging in live animals and humans and is widely used in preclinical and clinical research, drug development and medicine. FFNs incorporating radioactive fluorine isotope $F^{18}$ for use in PET imaging are described in PCT/US2009/000630 (WO 2009/097144), which is hereby incorporated by reference in its entirety.

Monoamine neurotransmitters are accumulated in synaptic vesicles by vesicular monoamine transporter 2 (VMAT2), which translocates the monoamine (e.g. dopamine) from cytosol to the lumen of synaptic vesicles. [5] Similarly, in chromaffin cells of adrenal medulla, epinephrine is accumulated in secretory vesicles by a closely related protein VMAT1 (FIG. 1). The vesicular lumen is acidic (pH~5-6) due to the action of vacuolar-$H^+$ ATPase, which imports $H^+$ at the expense of ATP hydrolysis. The pH gradient between the cytoplasm and the vesicular lumen in turn provides the driving force for the accumulation of neurotransmitters in the vesicles. Thus the pH gradient is one of the key parameters regulating synaptic plasticity as it controls the vesicle content and potentially the size of the releasable pool.

The pH gradient between the cytosol and the vesicular lumen is ATP dependent and thus closely coupled to the metabolic state of the presynaptic terminals. Despite the importance of this parameter there are currently no small molecule probes available for selective measurement of pH in synaptic or secretory vesicles. The pH-sensitive synaptopHluorin protein has been developed to measure pH in synaptic vesicles of cultured neurons. [6] Alternatively, construction of avidin-chimera proteins allow for anchoring a pH sensitive fluorescent dye, linked to biotin, to specific organelles including secretory vesicles. [7] These approaches, however, require transfection of the cell culture prior to measurement, or generation of transgenic animals for studies with tissue.

Commercially available pH-sensitive dyes (e.g. Lysotracker) [8] are not suitable for this task as they label other acidic organelles including endosomes and lysosomes, and in the brain they do not label presynaptic terminals. [9] Moreover, such dyes cannot measure pH within the synaptic vesicles in the brain.

Pancreatic β-cells, just like chromaffin cells, contain VMAT on the plasma membrane of their secretory vesicles. [$C^{11}$]DTBZ or fluoropropyl-9-desmethyl-DTBZ are used to determine the amount of VMAT, thus enabling researchers to determine the amount of pancreatic β-cells. But neither [$C^{11}$]DTBZ nor fluoropropyl-9-desmethyl-DTBZ are suitable for imaging dynamic changes in transmitter pools.

Herein, pH responsive compounds and their use in optical in situ measurement of pH, including pH changes, are described.

SUMMARY OF THE INVENTION

This invention provides a compound having the following structure:

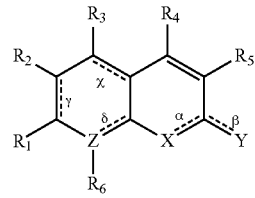

wherein

Y is O, X is O, bond α is absent and bond β is present, or
Y is H, X is CH, bond α is present, and bond β is absent;

atom Z is a carbon and bonds χ, δ and γ are present, or atom Z is a nitrogen and bonds χ, δ and γ are absent, or
atom Z is a nitrogen and bonds χ and δ are present and γ is absent;
$R_1$ is —OH, —O—$R_7$, or —O⁻,
  wherein $R_7$ is alkyl, alkenyl or alkynyl;
$R_2$ is —H, halogen, alkyl, alkenyl, alkynyl;
$R_3$ is —H, —OH, alkyl, alkenyl, alkynyl, or halogen;
or
$R_1$ is H, and $R_2$ together with $R_3$ form a substituted or unsubstituted aromatic ring;
$R_4$ is —H, —$CH_2CH_2NH_2$, or —$CH_2CH_2N(R_8)_2$;
  wherein $R_8$ is alkyl, alkoxycarbonyl, alkenyl, or alkynyl;
$R_5$ is —H, —$CH_2CH_2NH_2$, or —(C=O)$CH_2CH_2NH_2$, —$CH_2CH_2N(R_9)_2$;
  wherein $R_9$ is alkyl, alkoxycarbonyl, alkenyl, or alkynyl;
and
$R_6$ is H, alkyl, alkenyl, alkynyl, or halogen;
wherein each occurrence of alkyl, alkoxy, alkenyl, or alkynyl is substituted or unsubstituted, straight chain or branched;
or a pharmaceutically acceptable salt thereof.

This invention provides a process for preparing a compound having the structure

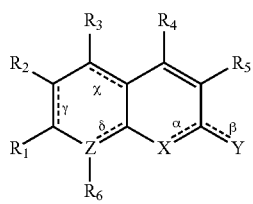

wherein
Y is O, X is O, bond α is absent and bond β is present, or
Y is H, X is CH, bond α is present, and bond β is absent;
atom Z is a carbon and bonds χ, δ and γ are present, or atom Z is a nitrogen and bonds χ, δ and γ are absent, or
atom Z is a nitrogen and bonds χ and δ are present and γ is absent;
$R_1$ is —OH, —O—$R_7$, or —O⁻,
  wherein $R_7$ is alkyl, alkenyl or alkynyl;
$R_2$ is —H, halogen, alkyl, alkenyl, alkynyl;
$R_3$ is —H, —OH, alkyl, alkenyl, alkynyl, or halogen;
or
$R_1$ is H, and $R_2$ together with $R_3$ form a substituted or unsubstituted aromatic ring;
$R_4$ is —H, —$CH_2CH_2NH_2$, or —$CH_2CH_2N(R_8)_2$;
  wherein $R_8$ is alkyl, alkoxycarbonyl, alkenyl, or alkynyl;
$R_5$ is —H, —$CH_2CH_2NH_2$, or —(C=O)$CH_2CH_2NH_2$, —$CH_2CH_2N(R_9)_2$;
  wherein $R_9$ is alkyl, alkoxycarbonyl, alkenyl, or alkynyl;
and
$R_6$ is H, alkyl, alkenyl, alkynyl, or halogen;
wherein each occurrence of alkyl, alkoxy, alkenyl, or alkynyl is substituted or unsubstituted, straight chain or branched;

comprising:
a) contacting a compound having the structure

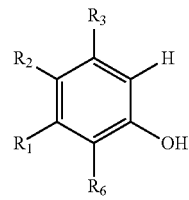

with a compound having the structure

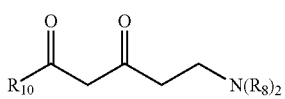

wherein $R_{10}$ is —OH, alkoxy, alkenyloxy, alkynyloxy, aryloxy, halogen, or heteroaryl,
  wherein each occurrence of alkoxy, alkenyloxy, alkynyloxy, aryloxy, and heteroaryl is substituted or unsubstituted;
or
a') contacting a compound having the structure

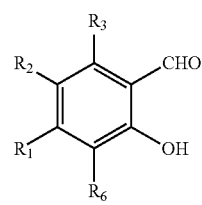

with a compound having the structure

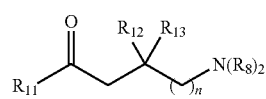

wherein $R_{11}$ is —OH, alkoxy, alkenyloxy, alkynyloxy, aryloxy, halogen, or heteroaryl;
$R_{12}$ and $R_{13}$ are each H or together form =O;
n is 1 or 2;
  wherein each occurrence of alkoxy, alkenyloxy, alkynyloxy, aryloxy, and heteroaryl is substituted or unsubstituted;
to form a compound having the structure

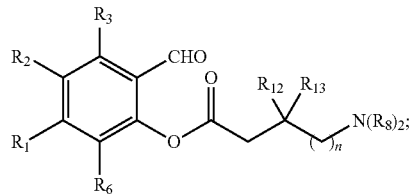

b') contacting the compound formed in step a') with a suitable base;
so as to prepare the compound.

This invention provides a method of determining the pH within a vesicle in a cell comprising:
   a) contacting the cell with any of the above compounds for a time sufficient for the compound to be taken up into the vesicle;
   b) quantitating fluorescence of the compound in the vesicle at a first excitation wavelength;
   c) quantitating fluorescence of the compound in the vesicle at a second excitation wavelength;
   wherein the ratio of the fluorescence quantitated in step b) and the fluorescence quantitated in step c) is compared to a predetermined reference curve so as to determine the pH within the vesicle in a cell.

This invention provides a method for detecting an active monoamine transporter in a sample comprising:
   a) providing a sample;
   b) quantitating fluorescence of the sample;
   c) contacting the sample with any of the above compounds for a time sufficient that an active monoamine transporter present in the sample can uptake the compound;
   d) washing the sample so as to remove any of the compound that has not been transported by the active monoamine transporter; and
   e) quantitating fluorescence of the sample,
   wherein an increase in the fluorescence of the sample quantitated in step e) over the fluorescence quantitated in step b) indicates the presence of an active monoamine transporter.

This invention provides a process of identifying a compound which is an inhibitor of a monoamine transporter comprising:
   a) providing a sample comprising a monoamine transporter in a medium;
   b) contacting the sample with any of the above compounds for a time sufficient that a monoamine transporter present in the sample can transport the compound;
   c) washing the sample so as to remove any of the compound that has not been transported by the monoamine transporter;
   d) quantitating fluorescence of the sample;
   e) contacting the sample with a compound to be tested for activity as an inhibitor of the monoamine transporter;
   f) contacting the sample with the compound as used in step b) under the same conditions set forth in step b);
   g) washing the sample so as to remove any of the compound that has not been transported by the monoamine transporter; and
   h) quantitating fluorescence of the sample,
   wherein no change in, or a decrease in, the fluorescence of the sample quantitated in step
   h) compared to step d) indicates that the test compound is an inhibitor of the monoamine transporter.

This invention provides a process of identifying a compound which is an enhancer of a monoamine transporter comprising:
   a) providing a sample comprising a monoamine transporter in a medium;
   b) contacting the sample with any of the above compounds for a time sufficient that a monoamine transporter present in the sample can transport the compound;
   c) washing the sample so as to remove any of the compound that has not been transported by the monoamine transporter;
   d) quantitating fluorescence of the sample;
   e) contacting the sample with a compound to be tested for activity as an enhancer of the monoamine transporter;
   f) contacting the sample with the compound as used in step b) under the same conditions set forth in step b);
   g) washing the sample so as to remove any of the compound that has not been transported by the monoamine transporter; and
   h) quantitating fluorescence of the sample,
   wherein an increase in the fluorescence of the sample quantitated in step h) compared to step d) indicates that the test compound is an enhancer of the monoamine transporter.

This invention provides a method of determining if neurotransmitter is released from a vesicle comprising:
   a) contacting the vesicle with any of the above compounds for a time sufficient for the compound to be taken up into the vesicle;
   b) quantitating fluorescence of the compound in the vesicle at a first excitation wavelength;
   c) quantitating fluorescence of the compound in the vesicle at a second excitation wavelength;
   d) subjecting the vesicle to a stimulus known to cause neurotransmitter release;
   e) quantitating fluorescence of the compound in the vesicle at a the excitation wavelength used in step b); and
   f) quantitating fluorescence of the compound in the vesicle at the excitation wavelength used in step c),
   wherein an increase in the ratio of fluorescence quantitated in step e) and fluorescence quantitated in step f) as compared to the ratio of fluorescence quantitated in step b) and fluorescence quantitated in step c) indicates that the neurotransmitter is released from the vesicle.

This invention further provides a method of determining if neurotransmitter is transported into a vesicle comprising:
   a) contacting the vesicle with any of the above compounds for a time sufficient for the compound to be taken up into the vesicle or synapse; and
   b) detecting fluorescence of the compound in the vesicle,
   wherein an increase in the fluorescence detected in the vesicle indicates that the neurotransmitter is transported into the vesicle.

DETAILED DESCRIPTION OF THE INVENTION

Figure 1:
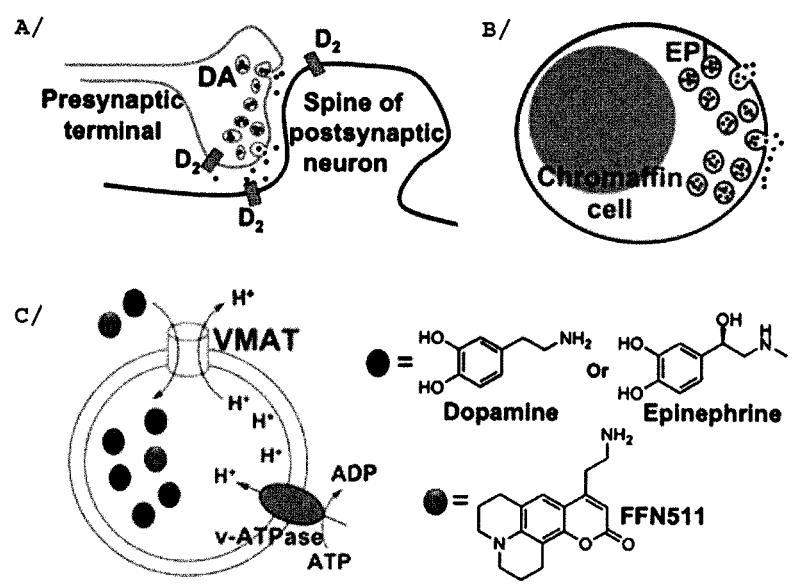
FIG. 1. Schematic illustration of (A) a dopaminergic presynaptic terminal connection to and modulating activity of the postsynaptic neuron (DA=dopamine, D2=dopamine receptor 2); (B) A chromaffin cell in adrenal medulla secreting epinephrine (EPI); (C) Vesicular uptake of endogenous substrates (dopamine or epinephrine) and exogenous fluorescent substrate (FFN511) by vesicular monoamine transporter (VMAT).

This invention provides a compound having the following structure:

wherein
Y is O, X is O, bond α is absent and bond β is present, or
Y is H, X is CH, bond α is present, and bond β is absent;

atom Z is a carbon and bonds χ, δ and γ are present, or atom Z is a nitrogen and bonds χ, δ and γ are absent, or
atom Z is a nitrogen and bonds χ and δ are present and γ is absent;

$R_1$ is —OH, —O—$R_7$, or —O⁻,
  wherein $R_7$ is alkyl, alkenyl or alkynyl;

$R_2$ is —H, halogen, alkyl, alkenyl, alkynyl;

$R_3$ is —H, —OH, alkyl, alkenyl, alkynyl, or halogen;

or $R_1$ is H, and $R_2$ together with $R_3$ form a substituted or unsubstituted aromatic ring;

$R_4$ is —H, —CH$_2$CH$_2$NH$_2$, or —CH$_2$CH$_2$N($R_8$)$_2$;
  wherein $R_8$ is alkyl, alkoxycarbonyl, alkenyl, or alkynyl;

$R_5$ is —H, —CH$_2$CH$_2$NH$_2$, or —(C═O)CH$_2$CH$_2$NH$_2$, —CH$_2$CH$_2$N($R_9$)$_2$;
  wherein $R_9$ is alkyl, alkoxycarbonyl, alkenyl, or alkynyl;

and $R_6$ is H, alkyl, alkenyl, alkynyl, or halogen;

wherein each occurrence of alkyl, alkoxy, alkenyl, or alkynyl is substituted or unsubstituted, straight chain or branched;

or a pharmaceutically acceptable salt thereof.

In an embodiment, $R_4$ is H or —CH$_2$CH$_2$NH$_2$; and $R_5$ is —H or —CH$_2$CH$_2$NH$_2$.

In another embodiment, $R_3$ is H or halogen.

In an embodiment, the compound has the structure:

-continued

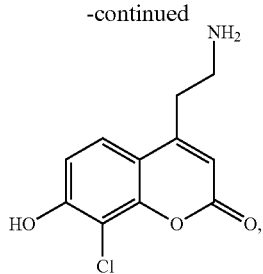

or a pharmaceutically acceptable salt thereof.

In another embodiment, the compound has the structure:

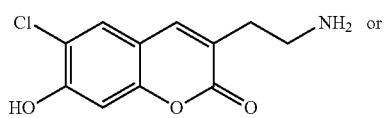

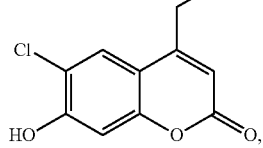

or a pharmaceutically acceptable salt thereof.

This invention provides a process for preparing a compound having the structure

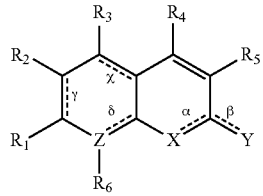

wherein
Y is O, X is O, bond α is absent and bond β is present, or
Y is H, X is CH, bond α is present, and bond β is absent;
atom Z is a carbon and bonds χ, δ and γ are present, or atom
  Z is a nitrogen and bonds χ, δ and γ are absent, or
atom Z is a nitrogen and bonds χ and δ are present and γ is
  absent;
$R_1$ is —OH, —O—$R_7$, or —O$^-$,
  wherein $R_7$ is alkyl, alkenyl or alkynyl;
$R_2$ is —H, halogen, alkyl, alkenyl, alkynyl;
$R_3$ is —H, —OH, alkyl, alkenyl, alkynyl, or halogen;
or
$R_1$ is H, and $R_2$ together with $R_3$ form a substituted or
  unsubstituted aromatic ring;
$R_4$ is —H, —CH$_2$CH$_2$NH$_2$, or —CH$_2$CH$_2$N($R_8$)$_2$;
  wherein $R_8$ is alkyl, alkoxycarbonyl, alkenyl, or alkynyl;
$R_5$ is —H, —CH$_2$CH$_2$NH$_2$, or —(C=O)CH$_2$CH$_2$NH$_2$,
  —CH$_2$CH$_2$N($R_9$)$_2$;
  wherein $R_9$ is alkyl, alkoxycarbonyl, alkenyl, or alkynyl;
and
$R_6$ is H, alkyl, alkenyl, alkynyl, or halogen;
wherein each occurrence of alkyl, alkoxy, alkenyl, or alkynyl is substituted or unsubstituted, straight chain or branched;

comprising:
a) contacting a compound having the structure

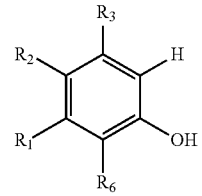

with a compound having the structure

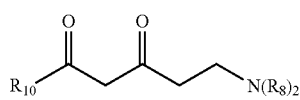

wherein $R_{10}$ is —OH, alkoxy, alkenyloxy, alkynyloxy,
  aryloxy, halogen, or heteroaryl,
  wherein each occurrence of alkoxy, alkenyloxy, alkynyloxy, aryloxy, and heteroaryl is substituted or unsubstituted;
or
a') contacting a compound having the structure

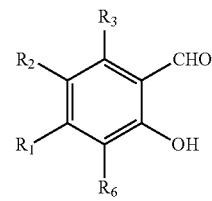

with a compound having the structure

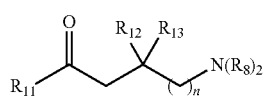

wherein $R_{11}$ is —OH, alkoxy, alkenyloxy, alkynyloxy,
  aryloxy, halogen, or heteroaryl;
$R_{12}$ and $R_{13}$ are each H or together form =O;
n is 1 or 2;
  wherein each occurrence of alkoxy, alkenyloxy, alkynyloxy, aryloxy, and heteroaryl is substituted or unsubstituted;
to form a compound having the structure

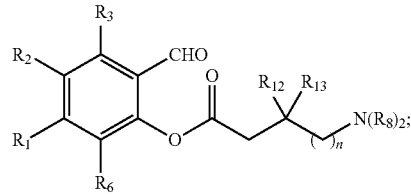

b') contacting the compound formed in step a') with a
  suitable base;
so as to prepare the compound.

In an embodiment, the process comprises:
a) contacting a compound having the structure

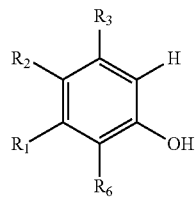

with a compound having the structure

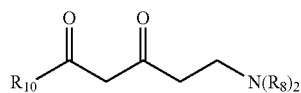

wherein $R_{10}$ is —OH, alkoxy, alkenyloxy, alkynyloxy, aryloxy, halogen, or heteroaryl,
  wherein each occurrence of alkoxy, alkenyloxy, alkynyloxy, aryloxy, and heteroaryl is substituted or unsubstituted.

In another embodiment, the process comprises:
a') contacting a compound having the structure

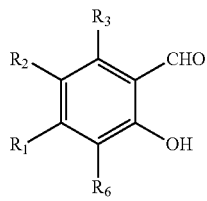

with a compound having the structure

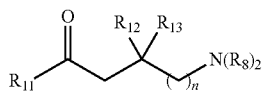

wherein $R_{11}$ is —OH, alkoxy, alkenyloxy, alkynyloxy, aryloxy, halogen, or heteroaryl;
$R_{12}$ and $R_{13}$ are each H or together form =O;
n is 1 or 2;
  wherein each occurrence of alkoxy, alkenyloxy, alkynyloxy, aryloxy, and heteroaryl is substituted or unsubstituted;
to form a compound having the structure

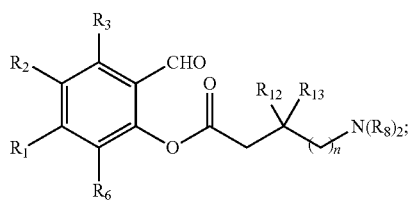

b') contacting the compound formed in step a') with a suitable base.

In an embodiment of the process, the compound prepared has the structure:

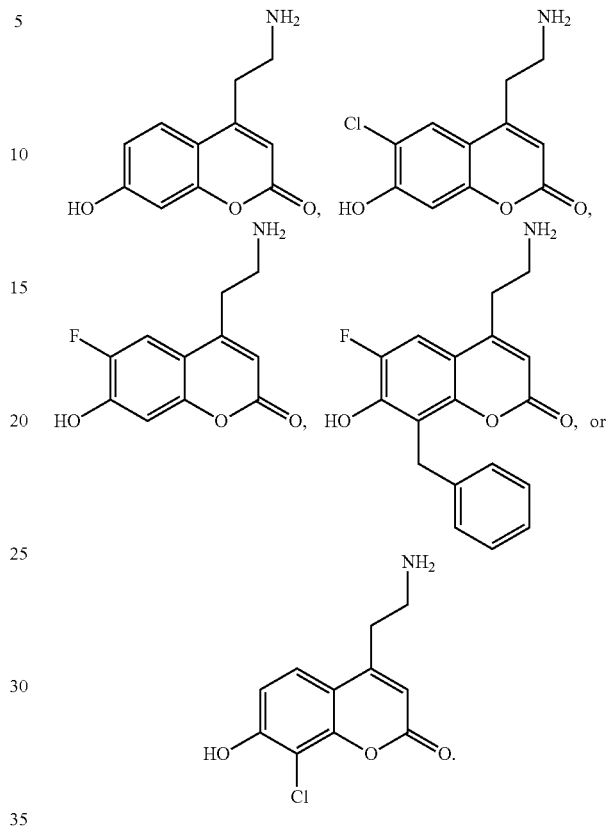

In another embodiment of the process, the compound prepared has the structure:

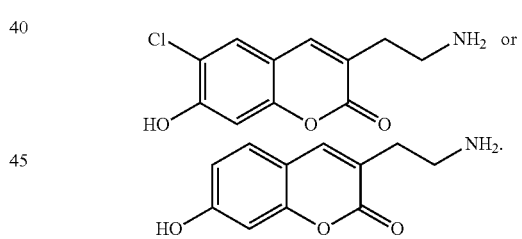

This invention provides a method of determining the pH within a vesicle in a cell comprising:
  a) contacting the cell with any of the above compounds for a time sufficient for the compound to be taken up into the vesicle;
  b) quantitating fluorescence of the compound in the vesicle at a first excitation wavelength;
  c) quantitating fluorescence of the compound in the vesicle at a second excitation wavelength;
  wherein the ratio of the fluorescence quantitated in step b) and the fluorescence quantitated in step c) is compared to a predetermined reference curve so as to determine the pH within the vesicle in a cell.

In an embodiment, the predetermined reference curve defines a correlation between the ratio of fluorescence at a first excitation wavelength and a second excitation wavelength of any of the above compounds; and the pH in a standardized sample.

In another embodiment of the method, the vesicle is a large dense core vesicle.

In an embodiment, the compound in step a) has the structure:

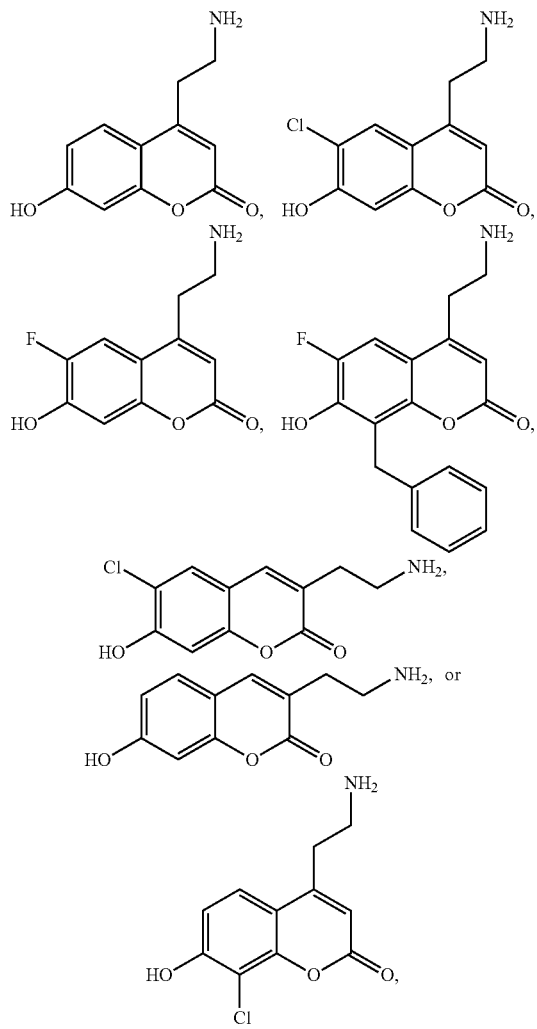

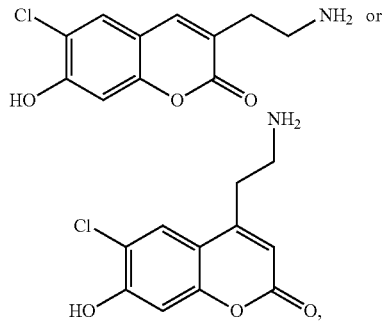

or a pharmaceutically acceptable salt thereof.

In another embodiment, the compound in step a) has the structure:

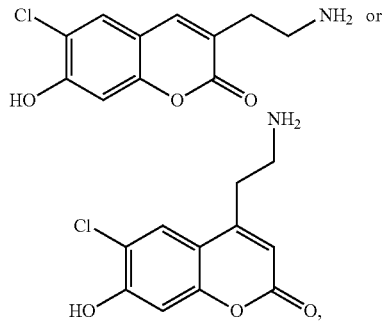

or a pharmaceutically acceptable salt thereof.

This invention provides a method for detecting an active monoamine transporter in a sample comprising:

a) providing a sample;
b) quantitating fluorescence of the sample;
c) contacting the sample with any of the above compounds for a time sufficient that an active monoamine transporter present in the sample can uptake the compound;
d) washing the sample so as to remove any of the compound that has not been transported by the active monoamine transporter; and
e) quantitating fluorescence of the sample, wherein an increase in the fluorescence of the sample quantitated in step e) over the fluorescence quantitated in step b) indicates the presence of an active monoamine transporter.

In an embodiment, the active monoamine transporter is vesicular monoamine transporter.

In another embodiment, the sample is a cell.

In an embodiment, the compound in step c) has the structure:

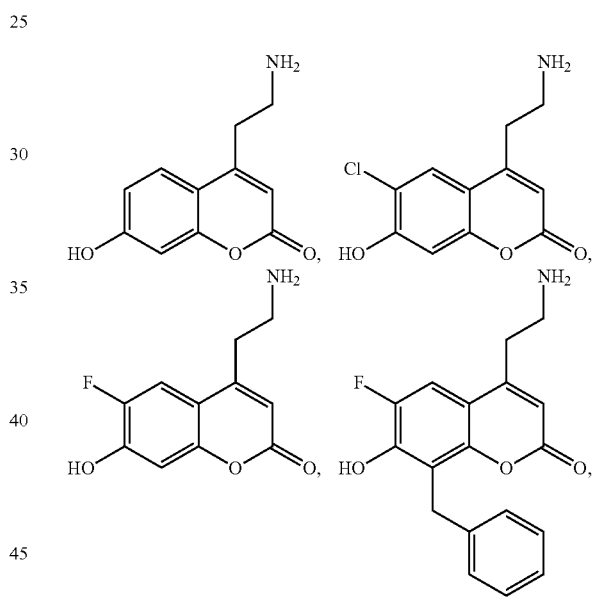

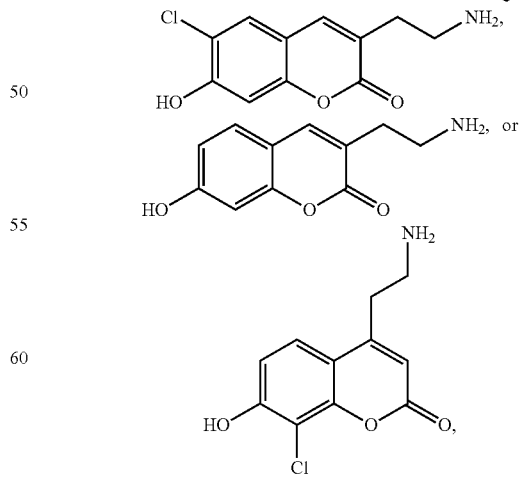

or a pharmaceutically acceptable salt thereof.

In another embodiment, the compound in step c) has the structure:

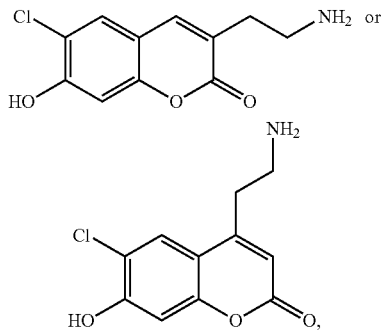

or a pharmaceutically acceptable salt thereof.

This invention provides a process of identifying a compound which is an inhibitor of a monoamine transporter comprising:
a) providing a sample comprising a monoamine transporter in a medium;
b) contacting the sample with any of the above compounds for a time sufficient that a monoamine transporter present in the sample can transport the compound;
c) washing the sample so as to remove any of the compound that has not been transported by the monoamine transporter;
d) quantitating fluorescence of the sample;
e) contacting the sample with a compound to be tested for activity as an inhibitor of the monoamine transporter;
f) contacting the sample with the compound as used in step b) under the same conditions set forth in step b);
g) washing the sample so as to remove any of the compound that has not been transported by the monoamine transporter; and
h) quantitating fluorescence of the sample,
wherein no change in, or a decrease in, the fluorescence of the sample quantitated in step
h) compared to step d) indicates that the test compound is an inhibitor of the monoamine transporter.

In an embodiment, the monoamine transporter is vesicular monoamine transporter.

In an embodiment, the compound in step b) has the structure:

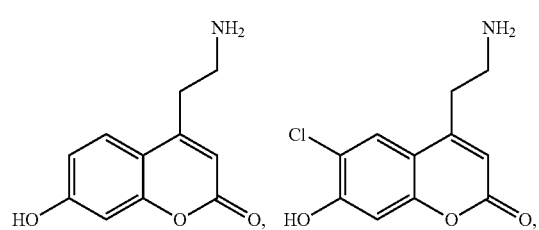

-continued

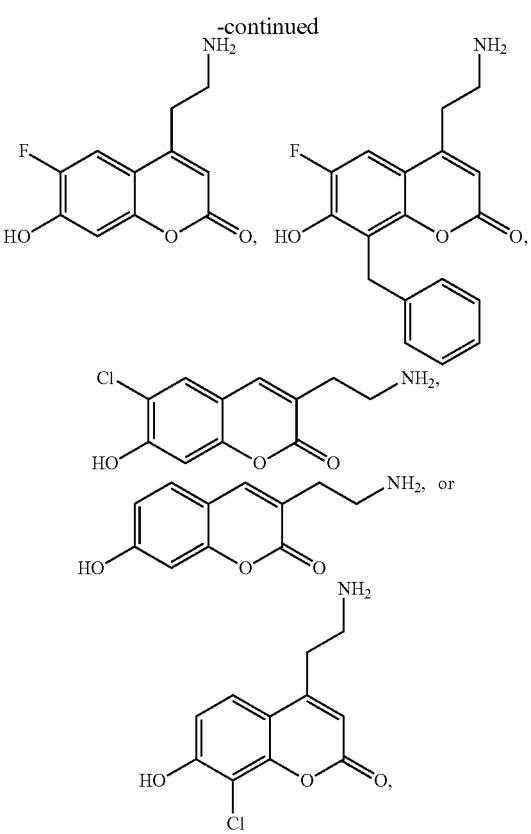

or a pharmaceutically acceptable salt thereof.

In another embodiment, the compound in step b) has the structure:

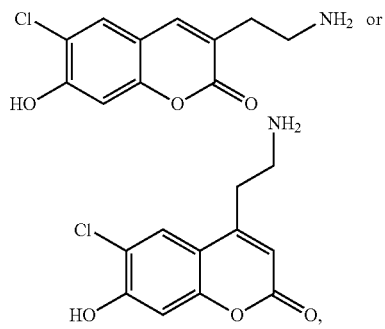

or a pharmaceutically acceptable salt thereof.

This invention provides a process of identifying a compound which is an enhancer of a monoamine transporter comprising:
a) providing a sample comprising a monoamine transporter in a medium;
b) contacting the sample with any of the above compounds for a time sufficient that a monoamine transporter present in the sample can transport the compound;
c) washing the sample so as to remove any of the compound that has not been transported by the monoamine transporter;
d) quantitating fluorescence of the sample;
e) contacting the sample with a compound to be tested for activity as an enhancer of the monoamine transporter;

f) contacting the sample with the compound as used in step b) under the same conditions set forth in step b);

g) washing the sample so as to remove any of the compound that has not been transported by the monoamine transporter; and h) quantitating fluorescence of the sample.

wherein an increase in the fluorescence of the sample quantitated in step h) compared to step d) indicates that the test compound is an enhancer of the monoamine transporter.

In an embodiment, the monoamine transporter is vesicular monoamine transporter.

In an embodiment, the compound in step b) has the structure:

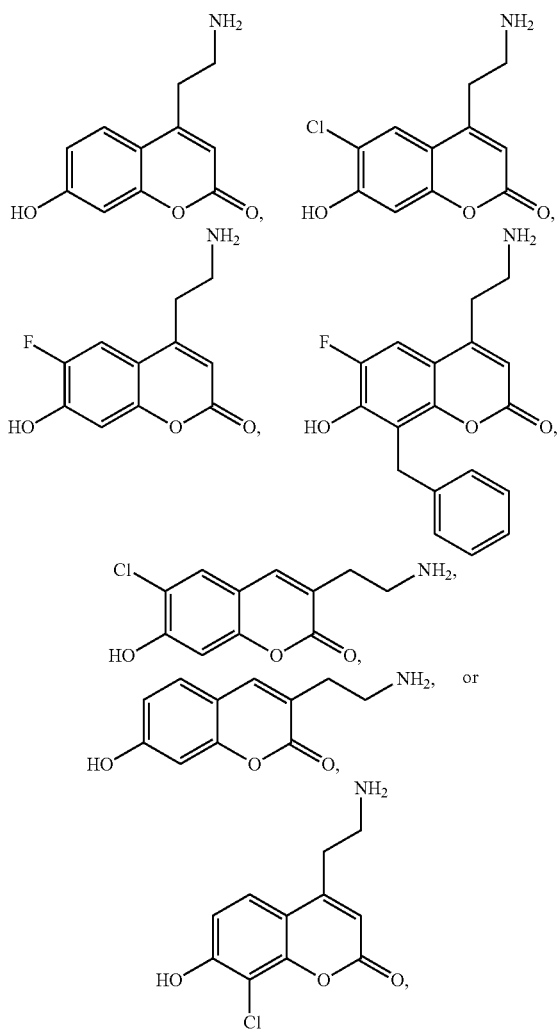

or a pharmaceutically acceptable salt thereof.

In another embodiment, the compound in step b) has the structure:

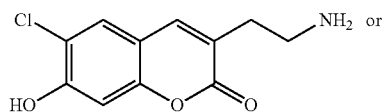

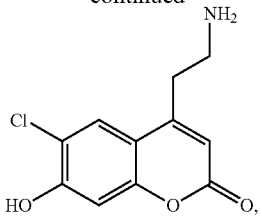

or a pharmaceutically acceptable salt thereof.

This invention provides a method of determining if neurotransmitter is released from a vesicle comprising:

a) contacting the vesicle with any of the above compounds for a time sufficient for the compound to be taken up into the vesicle;

b) quantitating fluorescence of the compound in the vesicle at a first excitation wavelength;

c) quantitating fluorescence of the compound in the vesicle at a second excitation wavelength;

d) subjecting the vesicle to a stimulus known to cause neurotransmitter release;

e) quantitating fluorescence of the compound in the vesicle at the first excitation wavelength used in step b); and f) quantitating fluorescence of the compound in the vesicle at the second excitation wavelength used in step c), wherein an increase in the ratio of fluorescence quantitated in step e) and fluorescence quantitated in step f) as compared to the ratio of fluorescence quantitated in step b) and fluorescence quantitated in step c) indicates that the neurotransmitter is released from the vesicle.

In an embodiment, the compound in step a) has the structure:

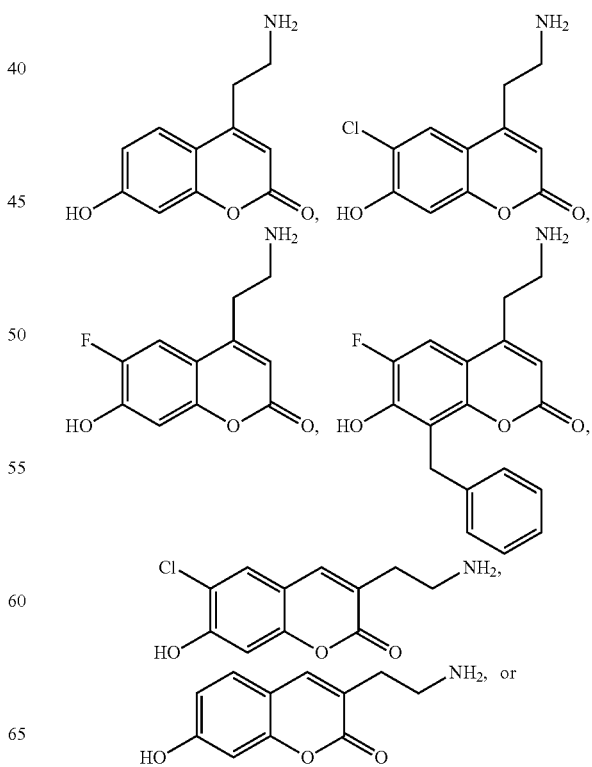

-continued

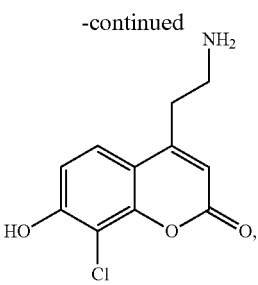

or a pharmaceutically acceptable salt thereof.

In another embodiment, the compound in step a) has the structure:

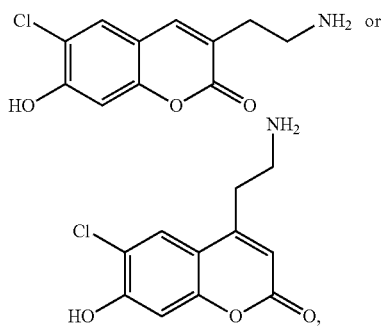

or a pharmaceutically acceptable salt thereof.

This invention further provides a method of determining if neurotransmitter is transported into a vesicle comprising:
  a) contacting the vesicle with any of the above compounds for a time sufficient for the compound to be taken up into the vesicle or synapse;
  b) detecting fluorescence of the compound in the vesicle; wherein an increase in the fluorescence detected in the vesicle indicates that the neurotransmitter is transported into the vesicle.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

It will be noted that the structure of the compounds of this invention includes an asymmetric carbon atom and thus the compounds occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wiley, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n-1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butyryl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise.

In the compounds of the present invention, alkyl, alkenyl, alkynyl, aryl, heterocyclyl and heteroaryl groups can be further substituted by replacing one or more hydrogen atoms be alternative non-hydrogen groups. These include, but are not limited to, halo, hydroxy, mercapto, amino, carboxy, cyano and carbamoyl.

The term "substituted" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and, in particular, halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, "pH" refers to the measure of the acidity or alkalinity of a solution. pH is formally dependent upon the activity of hydronium ions ($H_3O+$), also referred to as hydrogen ions ($H^+$), but for very dilute solutions, the molarity of $H_3O+$ may be used as a substitute with little loss of accuracy. Aqueous solutions at 25° C. with a pH less than 7.0 are considered acidic, while those with a pH greater than 7.0 are considered basic (alkaline). When a pH level is 7.0, it is defined as 'neutral' at 25° C. because at this pH the concentration of $H_3O^+$ equals the concentration of OH— in pure water.

The term "acid" refers to acids under both the Bronsted-Lowry and the Lewis definitions of acids. Under the Bronsted-Lowry definition, acids are defined as proton ($H^+$) donors. Examples of Bronsted-Lowry acids include, but are not limited to, inorganic acids such as hydrofluoric, hydrochloric, hydrobromic, hydroiodic, perchloric, hypochlorous, sulfuric, sulfurous, sulfamic, phosphoric, phosphorous, nitric, nitrous, and the like; and organic acids such as formic, acetic, trifluoroacetic, p-toluenesulfonic, camphorsulfonic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, methanesulfonic, ethane disulfonic, oxalic, isethionic, and the like. Under the Lewis definition, an acid is an electron acceptor capable of accepting electron density by virtue of possessing unoccupied orbitals. Examples of Lewis acids include, but are not limited to, metal salts such as $AlCl_3$, $FeCl_3$, $FeCl_3.SiO_2$, $CrCl_2$, $HgCl_2$, CuCl, $TiCl_4$, $Yb(OTf)_3$, InOTf, $TiCl_2(OiPr)_2$, and $Ti(OiPr)_4$; organometallic species such as trimethylaluminum and dimethylaluminum chloride; and boron species such as $BH_3$, $B(Et)_3$, $BF_3$, $BF_3$—$OEt_2$, $BBr_3$, $B(OMe)_3$, and $B(OiPr)_3$.

Examples of bases include, but are not limited to, alkali metal hydroxides, such as lithium hydroxide, sodium hydroxide, potassium hydroxide, and cesium hydroxide; alkali metal alkoxides, such as sodium methoxide, sodium ethoxide, sodium isopropoxide, sodium tert-butoxide, potassium tert-butoxide, lithium methoxide; alkali metal hydrides, such as lithium hydride, sodium hydride, and potassium hydride; alkali metal bicarbonates and carbonates, such as sodium bicarbonate, sodium carbonate, lithium bicarbonate, lithium carbonate, potassium carbonate, potassium bicarbonate, cesium carbonate, and cesium bicarbonate; organolithium bases, such as methyllithium, n-butyllithium, s-butyllithium, tert-butyllithium, isobutyllithium, phenyllithium, ethyllithium, n-hexyllithium, and isopropyllithium; amide bases, such as lithium amide, sodium amide, potassium amide, lithium hexamethyldisilazide, sodium hexamethyldisilazide, potassium hexamethyldisilazide, lithium diisopropylamide, lithium diethylamide, lithium dicyclohexylamide, and lithium 2,2,6,6-tetramethylpiperidide; and amine bases, such as pyridine, 4-(dimethylamino)pyridine, trimethylamine, diethylamine, triethylamine, diisopropylethylamine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), and the like.

As used herein, abbreviations are defined as follows:
Ac=acetyl
4-DMAP=4-(dimethylamino)pyridine
DMF=N,N-dimethylformamide
EDC=N-ethyl-N'-(3-dimethylaminopropyl)carbodiimide
TBAF=tetra-n-butylammonium fluoride
TBS=tert-butyldimethylsilyl
TMS=trimethylsilyl
Tf=trifluoromethanesulfonyl
KHMDS=potassium bis(trimethylsilyl)amide or potassium hexamethyldisilazide
AIBN=1,1'-azobisisobutyronitrile
9-BBN=9-borabicyclo[3.3.1]nonane
DIBA=diisobutylaluminum
THF=tetrahydrofuran
MeOH=methanol
DCE=1,2-dichloroethane
Ph=phenyl
Me=methyl
Et=ethyl
iPr=isopropyl
n-Bu=n-butyl
i-Bu=isobutyl
s-Bu=sec-butyl
t-Bu=tert-butyl
Ms=methanesulfonyl
Ts=p-toluenesulfonyl
SET=single electron transfer In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The term "fluorescence" refers to the emission of light of a particular wavelength (emission wavelength or $\lambda_{em}$) by a substance that has been excited with light of a different wavelength(s) ($\lambda_{ex}$). In most cases, absorption of light of a smaller wavelength (higher energy) induces emission of light with a larger (less energetic) wavelength. The energy difference between the absorbed and emitted photons is dissipated in the fluorescent material, via internal molecular vibrations and eventually heat.

As used herein, an "increase in fluorescence" of a compound means an increase in the measured level of fluorescence of the compound when the compound is excited with light of a predetermined excitation wavelength(s), or more specifically the emission intensity is directly proportional to brightness. In this case, brightness=$(\epsilon)(\Phi)$, where $\epsilon$ is the extinction coefficient at which the quantum yield is measured and $\Phi$ is the quantum yield. Similarly, a "decrease in fluorescence" of a compound means a decrease in the measured level of fluorescence of the compound when the compound is excited with light of a predetermined excitation wavelength(s), or more specifically the emission intensity is directly proportional to brightness.

Fluorescence may be quantitated with any of the many devices known to those of ordinary skill in the art, including, but not limited to photomultipliers, photometers, fluorimeters, CCD-based cameras or optic fiber systems and using fluorescent microscopy. Alternatively, fluorescence may be quantitated by the naked eye with or without the use of a microscope system. Fluorescence may be quantitated in arbitrary units.

As used herein, "reference standard" means a normalized value obtained form a standardized sample, and in the case of fluorescence means the normalized fluorescence measured from a sample obtained from a subject without a monoamine transporter deficiency (e.g. VMAT, DAT, SERT or NET) or without impaired monoamine transporter activity, or other standardized sample, as measured by a parallel assay with the same steps and conditions to which the tested sample is being subjected.

As used herein, "reference curve" means a normalized curve defining a correlation between at least two known and measurable properties obtained from a standardized sample. For example, the fluorescence measured from a sample without a monoamine transporter deficiency (e.g. VMAT, DAT, SERT or NET) or without impaired monoamine transporter activity, or other standardized sample, as measured by a parallel assay with the same steps and conditions to which the tested sample is being subjected, can be correlated with another known and measurable property, such as pH, of the standardized sample.

As used herein "physiological medium" means any natural or artificially synthesized medium recognizable by one of ordinary skill in the art as supporting monoamine transport activity in the presence of a monoamine. Examples of such include interstitial fluid, cerebrospinal fluid, and phosphate buffered saline.

VMAT as used herein, unless otherwise specified, refers to all VMAT forms, e.g. VMAT1 and VMAT2.

As used herein, a "competitive substrate" in relation to a monoamine transporter is a substance capable of binding to the monoamine transporter's active site in place of the physiological substrate and being transported.

As used herein, a "competitive inhibitor" in relation to a monoamine transporter is a substance capable of binding to the monoamine transporter's active site in place of the physiological substrate but not transported.

As used herein, "diagnosing" a monoamine transporter (e.g. VMAT, DAT, SERT or NET) deficiency or a disease associated with such, means identifying a cell, a tissue, or a sample as having impaired monoamine transporter activity below the level of activity of that monoamine transporter in a non-pathological or non-diseased cell, tissue or sample.

Characteristics of psychiatric disease states associated with impaired monoamine transport are described in Diagnostic and Statistical Manual of Mental Disorders DSM-IV-TR Fourth Edition by the American Psychiatric Association, American Psychiatric Publishing, 4th edition (June 2000), herein incorporated by reference.

As used herein "neurotransmitter release" shall mean the release, e.g. by exocytosis, of a neurotransmitter from a synaptic vesicle into, for example, a synaptic cleft.

As used herein "neurotransmitter uptake" shall mean the uptake of a neurotransmitter from, for example, a synaptic cleft into a pre- or post-synaptic terminal (i.e. includes what is termed re-uptake), a glial cell, or any cell comprising a monoamine transporter; or the uptake of a neurotransmitter into a synaptic vesicle.

The methods of the present invention when pertaining to cells, and samples derived or purified therefrom, including monoamine transporter containing fractions, may be performed in vitro. The methods of diagnosis may, in different embodiments, be performed in vivo, in situ, or in vitro. The methods of diagnosis may be performed on human, or non-human mammalian subjects.

The various probes described herein may be monoamine transporter competitive substrates or inhibitors, and may be antagonists or agonists of the monoamine receptors. For example, the probes disclosed herein may serotoninmimetic or dopamimetic.

A "sample" as used herein means a biological material including, but not limited to, a liquid, coma, a cell, a tissue (including blood), or a derivative thereof including, but not limited to, a fraction, a centrifugate, a cellular component, a tissue slice, or a disaggregated tissue, each expected to contain a monoamine transporter.

Such a sample may be removed from a subject, or if stated, may be in situ.

"Mammalian nervous tissue" includes peripheral and central nervous tissue. Examples of nerves tissue include but are not limited to disaggregated cells, cultured cells and slices of tissue such as hippocampal or substantia nigral.

The compounds of the instant invention may be in a salt form. As used herein, a "salt" is a salt of the instant compounds which has been modified by making acid or base salts of the compounds. In the case of compounds used for treatment of cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compositions of this invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds may comprise a single compound or mixtures thereof with anti-cancer compounds, or tumor growth inhibiting compounds, or with other compounds also used to treat neurite damage. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the cancer, all using dosage forms well known to those of ordinary skill in the pharmaceutical arts.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989): Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds may also be coupled to soluble polymers as targetable drug carriers or as a prodrug. Such polymers include polyvinylpyrrolidone, pyran copolymer, polyhydroxypropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds of the instant invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the invention can be coated onto stents for temporary or permanent implantation into the cardiovascular system of a subject.

Below, compounds of the present invention are synthesized according to the general procedure shown in Scheme 1. The "R" groups shown in Scheme 1 and in subsequent schemes denote any number of generic substituents, such as those described hereinabove. "LG" indicates a suitable leaving group. Suitable leaving groups include, but are not limited to, hydroxy, alkoxy, alkenyloxy, alkynyloxy, aryloxy, halogen, or heteroaryl groups.

"PG" indicates a suitable protecting group for the functionality intended to be protected. The use of protecting groups in organic synthesis is well-known to those skilled in the art of organic synthesis. Various protecting groups and methods of using them may be found in Wuts, P. G. M.; Greene, T.; *Greene's Protective Groups in Organic Synthesis*, Wiley-Interscience, Fourth edition (Oct. 30, 2006), which is hereby incorporated by reference in its entirety.

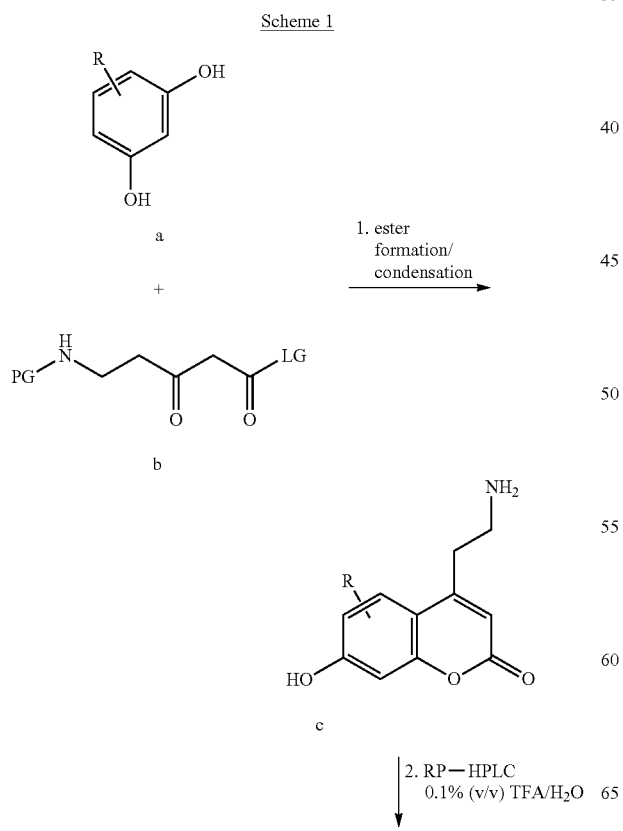

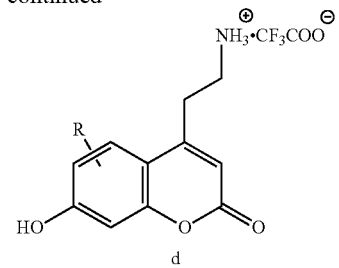

In general scheme 1, compounds having the structure of compound d are synthesized via ester formation followed by intra-molecular condensation of resorcinol a with beta-keto ester b.

Ester formation is achieved by any number of esterification reactions known to those having ordinary skill in the art. For example, coupling reagents including, but not limited to, 1,3-diisopropylcarbodiimide (DIC) and N,N'-dicyclohexylcarbodiimide (DCC) can be used in the presence of a suitable base when LG is hydroxy. As a further example, when LG is an alkoxy group, a suitable acid can be used.

The resulting coumarin c is purified by reversed-phase HPLC using an appropriate linear gradient of acetonitrile containing 10% de-ionized water and 0.1% (v/v) trifluoroacetic acid (TFA)/water to furnish TFA salt d.

Compounds of structure d may further be alkylated using alkylation methods known by those skilled in art of organic synthesis. For example, compound d is methylated via an Eschweiler-Clarke dimethylation reaction in the presence of formaldehyde and $NaBH(OAc)_3$, as shown in general scheme 2.

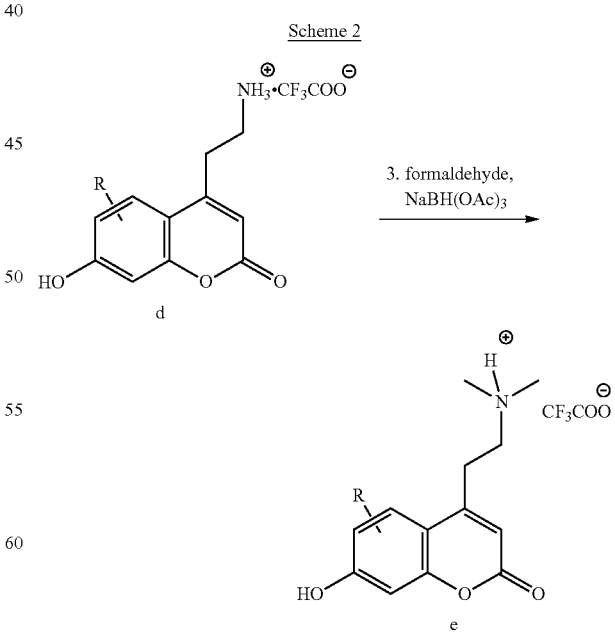

Compounds having the structure i are synthesized according to general scheme 3.

Scheme 3

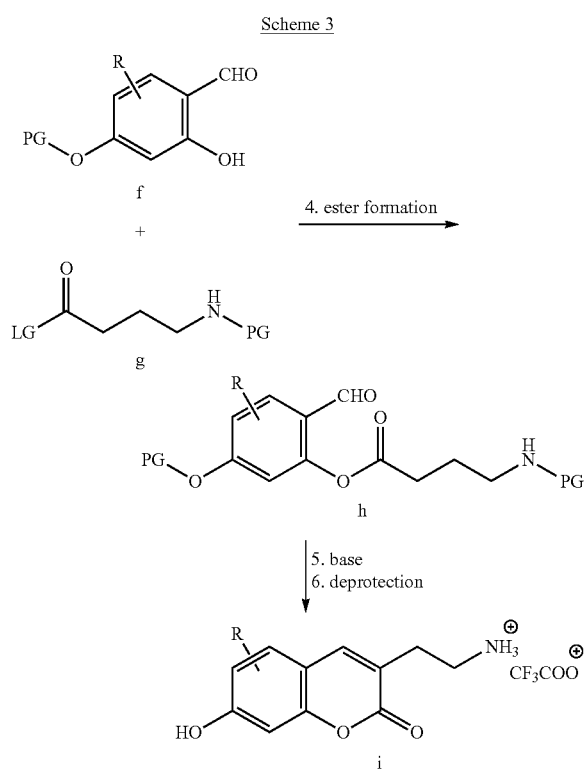

In general scheme 3, compounds of structure i are synthesized by reaction of mono-protected resorcinol f with acid g to form ester h in step 4. Subsequent reaction of h in the presence of a suitable base, followed by deprotection with TFA furnishes compound i.

Those having ordinary skill in the art of organic synthesis will appreciate that modifications to the general procedure shown in schemes 1, 2, and 3 can be made to yield structurally diverse coumarin compounds. For example, in scheme 1, resorcinol a may be obtained commercially with the desired substituents already in place. When the desired resorcinol starting material is not commercially available, substituents are installed onto the phenyl ring of the molecule using standard aryl substitution reactions well known in organic synthesis. Alternatively, compound a can be replaced by a naphthalenediol, such as 2,7-dihydroxynaphthalene.

In general scheme 3, additional substituent diversity is introduced by varying the length of the alkyl chain and/or the substituents along the alkyl chain of compound g. For example, additional carbonyl groups can be introduced on the alkyl chain of compound g.

In research, the compounds and compositions of the present invention are useful for examination of fundamental mechanisms (and their malfunction in diseases) controlling transmitter or hormone release in secretory cells (e.g., epinephrine release from chromaffin cells, insulin release in pancreatic beta-cells). They enable examination of pH changes in synaptic vesicles as an important physiological parameter contributing to synaptic plasticity (e.g., quantum size, a number of transmitter molecule released per vesicle fusion event), and pH changes in synaptic vesicles of presynaptic terminals in animal models of neuropsychiatric diseases. The control of pH in secretory vesicles is also important for proper processing of peptides and hormones such as insulin and endorphins, which may contribute to understanding a broad variety of metabolic disorders. The compounds and compositions of the present invention are useful in rodent brain slice preparation and in an intact fruit fly brain (*Drosophila melanogaster*).

In drug screening, the compounds and compositions of the present invention enable high throughput screening for VMAT2 and VMAT1 inhibitors, as well as neurotransmitter releasers, via cell fluorimetric assays. VMAT2 is a medicinal target for Huntington's disease and potentially for novel antidiabetes agents. Also, VMAT2 substrates act as neurotransmitter releasers, which exhibit a variety of activities and are used for treatment of several disorders (e.g., ADHD, drug addiction). In PC12 cells, central catecholamine and serotonin neurons, and chromaffin and beta cells, screens for compound toxicity is also possible [i.e., decrease in the pH gradient between the cytosol and the vesicle lumen can be a result of direct action of a lipophilic base (e.g. amphetamine), or inhibition of vacuolar-$H^+$ ATPase, or interference with metabolism and homeostasis of ATP], including drug candidates, pesticides and other agents.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Unless otherwise noted, all chemicals were purchased from Sigma-Aldrich or Strem and used without further purification. When necessary, solvents were dried by passing them through a column of alumina under argon. Flash chromatography was performed on SILICYCLE silica gel (230-400 mesh). Nuclear Magnetic Resonance spectra were recorded at 300 K (unless otherwise noted) on Bruker 300 or 400 Fourier transform NMR spectrometers. Proton chemical shifts are expressed in parts per million (ppm, δ scale) and are referenced to residual protium in the NMR solvent ($CDCl_3$, δ 7.26; $CD_3OD$, δ 3.30; DMSO, δ 2.49). Data for $^1H$ NMR are reported as follows: chemical shift, integration, multiplicity (s=singlet, d=doublet, t=triplet, m=multiplet, bs=broad singlet), and coupling constant in Hertz (Hz). Carbon chemical shifts are expressed in parts per million (ppm, δ scale) and are referenced to the carbon resonance of the NMR solvent ($CDCl_3$, δ 77.0; $CD_3OD$, δ 49.0; DMSO, δ 39.5). Mass spectra were recorded on a JEOL LCmate (ionization mode: APCI+) or on a JMSHX110 HF mass spectrometer (ionization mode: FAB+). Preparative HPLC was performed with a Waters 600 Controller on a Vydac C18 Protein & Peptide column (#218TP1022); fractions were detected with a Waters 2487 Dual λ Absorbance Detector and collected with a Waters 2767 Sample Manager. Data was analyzed using OpenLynx software. Isocratic elution or linear gradients of solvents A and B were used (A=HPLC grade acetonitrile or methanol containing 10% (v/v) de-ionized water (Millipore Simplicity 185, 18.2 M#); B=deionized water containing 0.1% (v/v) trifluoroacetic acid (ReagentPlus grade, 99%). Analytical HPLC was performed on a Vydac C18 Protein & Peptide column (#218TP54).

Example 1

Structure and Synthesis of Coumarin Probes

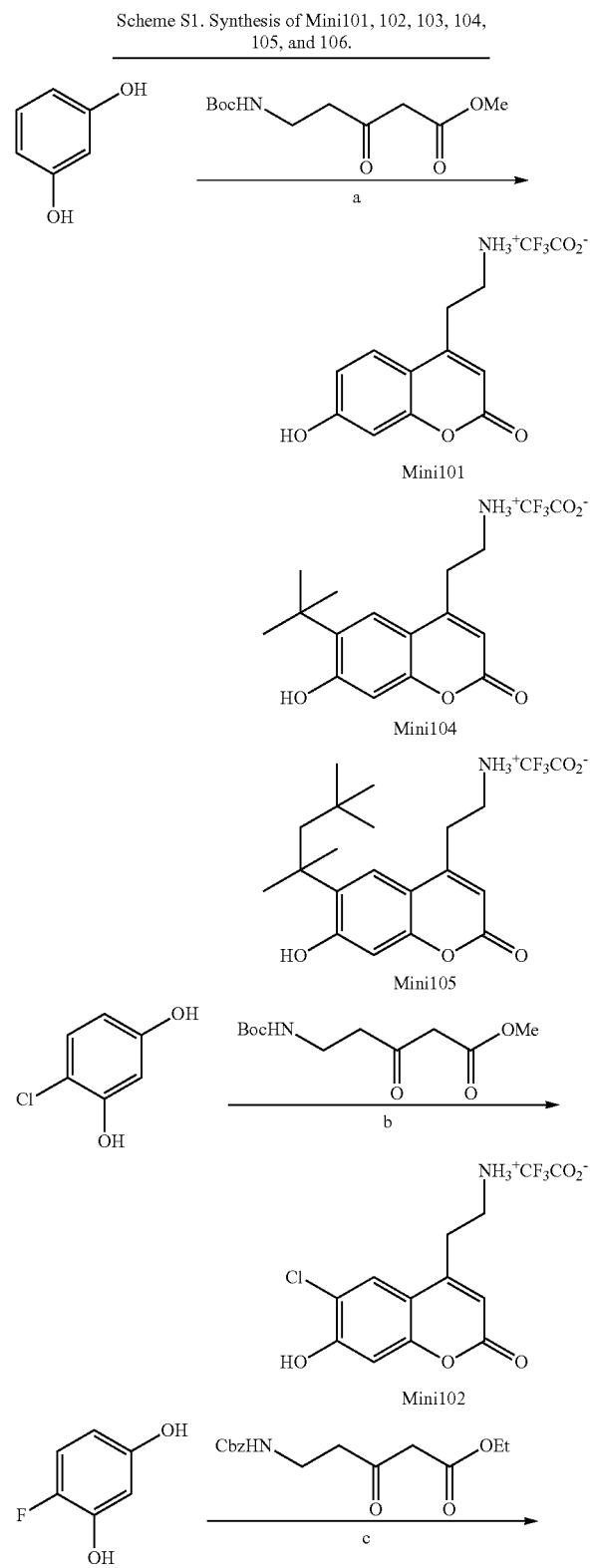
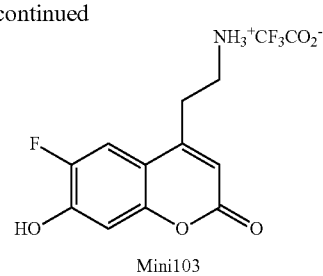
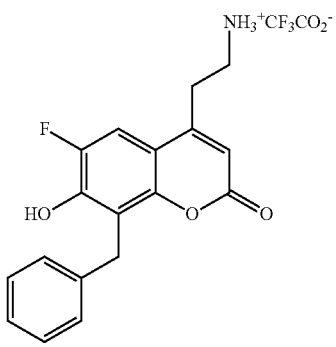
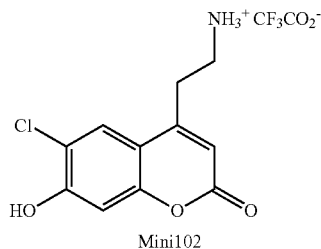

(a) MSA (Methanesulfonic acid), RT, 2 h, 63%, 28%, and 5% for Mini101, 104, and 105, respectively;
(b) MSA, RT, 3 h, 37%;
(c) MSA, RT, 3 h, 51% and 3% for Mini103 and Mini106, respectively.

Compound series of Mini101-106 were synthesized via a von Pechmann type condensation of resorcinols with β-ketoester 1 or 2 (prepared by following the published methods) [10, 11] in methanesulfonic acid [12, 13] for 2-3 hours at RT followed by purification by HPLC to obtain the probes as TFA salts. Synthesis of Mini102 is described below as a representative example.

To a mixture of 4-chlororesorcinol (0.17 g, 1.2 mmol) and 1 (0.20 g, 0.8 mmol) was added methanesulfonic acid (1.3 mL, 20 mmol) at 0° C. The clear brown solution gradually became dark orange within 3 h at which point the reaction mixture was diluted with cold ethyl ether (−20° C., 10 mL), and centrifuged (3000 rpm) at 4° C. for 20 min. After removing the ether solvent by aspiration, the residual orange solid was dried under high vacuum, dissolved in $H_2O$ (3 mL), and purified by RP-HPLC using an appropriate linear gradient of acetonitrile containing 10% de-ionized water (A) and 0.1% (v/v) $TFA/H_2O$.

(B) (3-50% A over 20 min. followed by a steep gradient to 100% A and equilibrium back to 3% A). The fractions containing the product (retention time ~12.7 min) were collected, concentrated, and lyophilized to give Mini102 as a white solid (37%). $^1$H NMR (DMSO-d6, 300 MHz): δ 11.55 (1H, bs), 7.86 (1H, s), 7.86 (3H, bs), 6.95 (1H, s), 6.25 (1H, s), 3.11

(2H, t, J=6.2 Hz), 3.03 (2H, t, J=6.0 Hz). $^{13}$C NMR (DMSO-d6, 75 MHz): δ 160.5, 157.4, 154.3, 151.9, 126.4, 118.0, 113.4, 112.5, 104.5, 38.4, 29.7. LRMS (APCI+): Calc'd for $C_{11}H_{10}ClNO_3$ 239.0 m/z, measured 240.2 (MH+).

Mini101

$^1$H NMR (DMSO-d6, 300 MHz): δ 10.65 (1H, s), 7.84 (3H, bs), 7.65 (1H, d, J=8.8 Hz), 6.83 (1H, dd, J=8.7, 2.4 Hz), 6.75 (1H, d, J=2.3 Hz), 6.18 (1H, s), 3.19-3.09 (2H, m), 3.02 (2H, t, J=6.8 Hz). $^{13}$C NMR (DMSO-d6, 75 MHz): δ 162.2, 161.0, 156.1, 152.7, 127.0, 113.9, 112.1, 111.7, 103.4, 38.3, 29.8. LRMS (APCI+): Calc'd for $C_{11}H_{11}NO_3$ 205.1 m/z, measured 206.1 (MH+).

Mini103

$^1$H NMR (DMSO-d6, 300 MHz): δ 11.26 (1H, bs), 7.93 (3H, s), 7.68 (1H, d, J=11.8 Hz), 6.95 (1H, d, J=7.5 Hz), 6.26 (1H, s), 3.12 (2H, t, J=6.6 Hz), 3.01 (2H, t, J=6.6 Hz). $^{13}$C NMR (DMSO-d6, 75 MHz): δ 159.9, 151.1 (d, J=45.2 Hz), 149.8, 149.2 (d, J=14.4 Hz), 112.6, 111.4, 111.1, 110.2 (d, J=7.3 Hz), 104.9, 37.5, 29.0. LRMS (APCI+): Calc'd for $C_{11}H_{10}FNO_3$ 223.1 m/z, measured 224.3 (MH+).

Mini104

$^1$H NMR (DMSO-d6, 300 MHz): δ 10.73 (1H, s), 7.88 (3H, bs), 7.40 (1H, s), 6.79 (1H, s), 6.15 (1H, s), 3.22-3.12 (2H, m), 3.07 (2H, t, J=6.9 Hz), 1.39 (9H, s). $^{13}$C NMR (DMSO-d6, 75 MHz): δ 160.2, 160.0, 153.2, 152.0, 133.3, 121.9, 110.7, 109.9, 103.1, 37.3, 34.4, 29.2, 28.6. LRMS (APCI+): Calc'd for $C_{15}H_{19}NO_3$ 261.1 m/z, measured 262.1 (MH+).

Mini105

$^1$H NMR (DMSO-d6, 300 MHz): δ 10.67 (1H, s), 7.83 (3H, bs), 7.40 (1H, s), 6.74 (1H, s), 6.15 (1H, s), 3.22-3.03 (4H, m), 1.96 (2H, s), 1.43 (6H, s), 0.72 (9H, s). $^{13}$C NMR (DMSO-d6, 75 MHz): δ 160.5, 160.1, 153.2, 152.0, 132.5, 122.8, 110.6, 110.0, 102.9, 51.2, 38.5, 37.3, 32.0, 31.2, 30.8, 28.6. LRMS (APCI+): Calc'd for $C_{19}H_{27}NO_3$ 317.2 m/z, measured 318.0 (MH+).

Mini106

$^1$H NMR (CD$_3$OD, 300 MHz): δ 7.49 (2H, d, J=11.2 Hz), 7.37-7.34 (2H, m), 7.23-7.12 (H, m), 6.26 (1H, s), 4.20 (2H, s), 3.27 (2H, t, J=7.8 Hz), 3.10 (2H, t, J=7.5 Hz). $^{13}$C NMR (CD$_3$OD, 75 MHz): δ 162.7, 153.3, 151.9, 151.2 (d, J=97.1 Hz), 148.7 (d, J=3.6 Hz), 148.4, 141.0, 129.7, 129.2, 127.1, 120.2, 113.4, 111.7 (d, J=7.7 Hz), 109.2 (d, J=22.4 Hz), 39.1, 30.5, 29.6. LRMS (APCI+): Calc'd for $C_{18}H_{16}FNO_3$ 313.1 m/z, measured 314.3 (MH+).

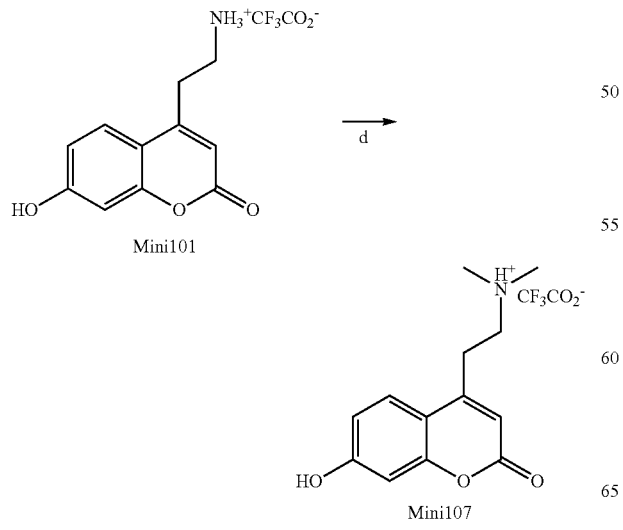

(d) formaldehyde (~37 wt. % in H$_2$O), NaBH(OAc)$_3$, CH$_2$Cl$_2$, RT, 6 h, 40%;
(e) formaldehyde (~37 wt. % in H$_2$O), NaBH(OAc), CH$_2$Cl$_2$, RT, 12 h, 76%;
(f) formaldehyde (~37 wt. % in H$_2$O), NaBH(OAc), CH$_2$Cl$_2$, RT, 15 h, 51%.

Compound series of Mini107-109 were synthesized via Eschweiler-Clarke dimethylation of Mini101-103 in dichloromethane with formaldehyde and NaBH(OAc)$_3$. The reaction mixture was stirred for the indicated time (Scheme S2) at room temperature. Purification by HPLC provided the probes as TFA salts. Synthesis of Mini107 is described below as a representative example.

To Mini101 (40 mg, 0.13 mmol) in CH$_2$Cl$_2$ (5 mL, 0.026 M) were added formaldehyde (~37 wt. % in H$_2$O, 0.20 g, 2.5 mmol) and NaBH(OAc)$_3$ (1.3 g, 6.1 mmol). The reaction solution was stirred for 6 h at RT, and the crude mixture was extracted into H$_2$O (2×2 mL) and purified by RP-HPLC using an appropriate linear gradient of acetonitrile containing 10% de-ionized water (A) and 0.1% (v/v) TFA/H$_2$O (B) (3-25% A over 30 min followed by a steep gradient to 100% A and equilibrium back to 3% A). The fractions containing the product (retention time ~18.1 min) were collected, concentrated, and lyophilized to give Mini107 as a white solid (40%). $^1$H NMR (DMSO-d6, 300 MHz): δ 10.76 (1H, bs), 9.85 (1H, bs), 7.71 (1H, d, J=8.8 Hz), 6.84 (1H, dd, J=8.7, 2.4 Hz), 6.75 (1H, d, J=2.3 Hz), 6.21 (1H, s), 3.40 (2H, t, J=7.5 Hz), 3.15 (2H, t, J=7.5 Hz), 2.87 (6H, s). 13C NMR (DMSO-d6, 100 MHz): δ 161.5, 160.1, 155.2, 151.9, 126.4, 113.1, 110.7, 110.6, 102.6, 54.6, 42.4, 25.8. LRMS (APCI+): Calc'd for C$_{13}$H$_{15}$NO$_3$ 233.1 m/z, measured 234.2 (MH+).

Mini108

$^1$H NMR (DMSO-d6, 400 MHz): δ 11.54 (1H, bs), 9.58 (1H, bs), 7.92 (1H, s), 6.94 (1H, s), 6.28 (1H, s), 3.47-3.33 (2H, m), 3.16 (2H, t, J=8.0 Hz), 2.88 (6H, s). $^{13}$C NMR (DMSO-d6, 100 MHz): δ 159.6, 156.6, 153.3, 151.1, 125.8, 117.3, 111.7, 111.6, 103.6, 54.4, 42.4, 25.6. LRMS (APCI+): Calc'd for C$_{13}$H$_{14}$ClNO$_3$ 267.1 m/z, measured 268.2 (MH+).

Mini109

$^1$H NMR (DMSO-d6, 400 MHz): δ 11.23 (1H, bs), 9.51 (1H, bs), 7.75 (1H, d, J=11.8 Hz), 6.96 (1H, d, J=7.5 Hz), 6.30 (1H, s), 3.46-3.34 (2H, m), 3.13 (2H, t, J=8.0 Hz), 2.88 (6H, s). $^{13}$C NMR (CD3OD, 75 MHz): δ 162.7, 161.8 (d, J=73.2 Hz), 152.6 (d, J=8.0 Hz), 151.9, 151.3 (d, J=15.1 Hz), 148.8, 113.0, 111.9 (d, J=21.7 Hz), 106.3, 56.6, 43.7, 27.5. LRMS (APCI+): Calc'd for C$_{13}$H$_{14}$FNO$_3$ 251.1 m/z, measured 252.2 (MH+).

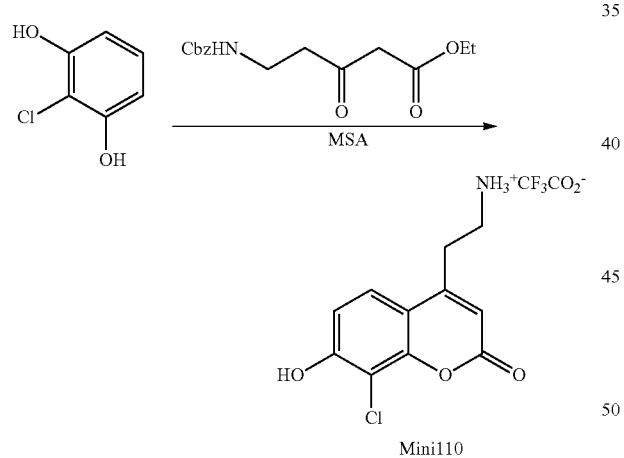

Compound Mini110 is synthesized using the following procedure.

To a mixture of 2-chlororesorcinol (0.17 g, 1.2 mmol) and 2 (0.20 g, 0.8 mmol) was added methanesulfonic acid (1.3 mL, 20 mmol) at 0° C. The clear brown solution gradually became dark orange within 3 h at which point the reaction mixture was diluted with cold ethyl ether (−20° C., 10 mL), and centrifuged (3000 rpm) at 4° C. for 20 min. After removing the ether solvent by aspiration, the residual orange solid was dried under high vacuum, dissolved in H2O (3 mL), and purified by RP-HPLC using an appropriate linear gradient of acetonitrile containing 10% de-ionized water (A) and 0.1% (v/v) TFA/H2O (B) (3-50% A over 20 min followed by a steep gradient to 100% A and equilibrium back to 3% A). The fractions containing the product were collected, concentrated, and lyophilized to give Mini110 as a white solid (~60%).

Figure 13:
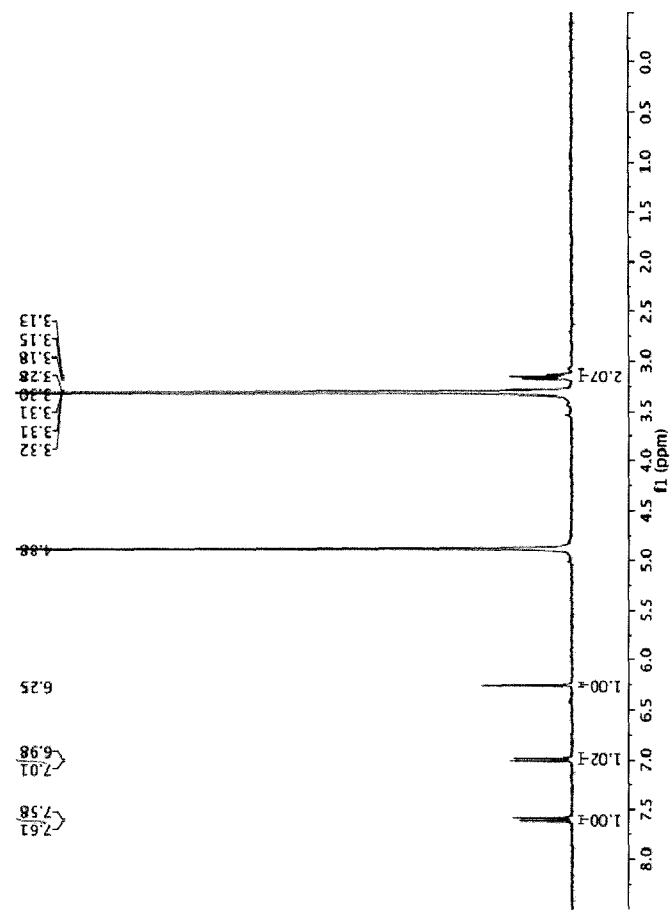
FIG. 13. NMR spectrum of compound Mini110.

NMR analysis of Mini110 is shown in FIG. 13.

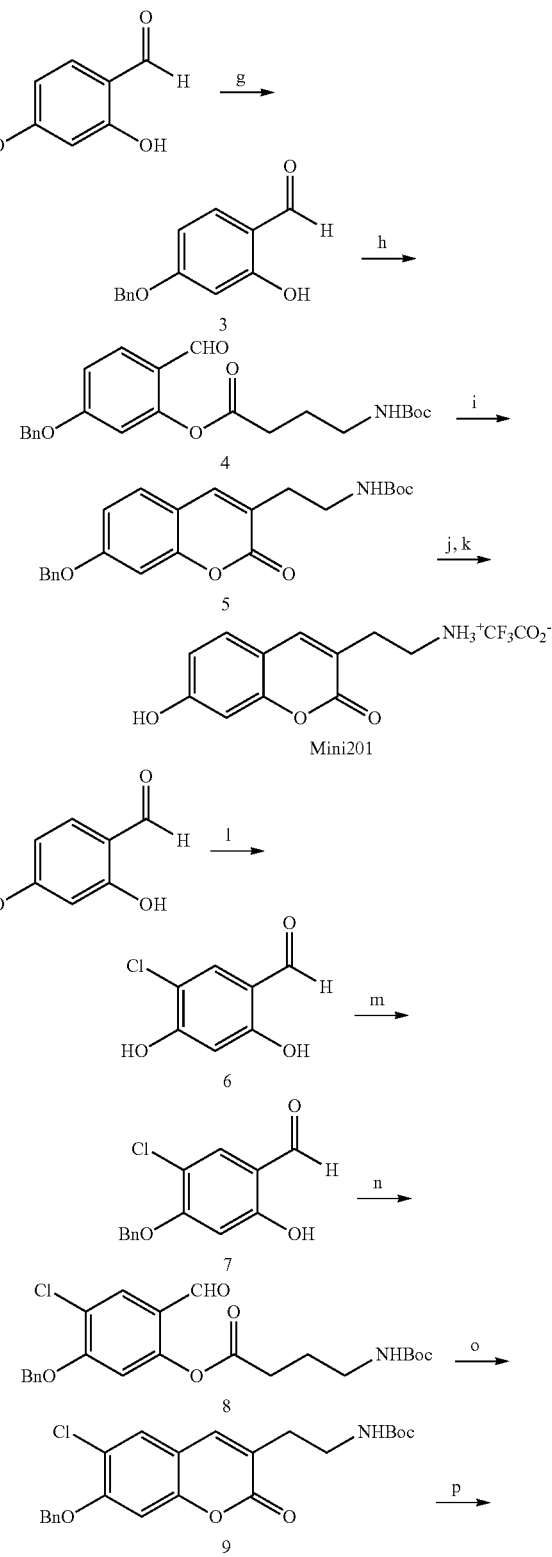

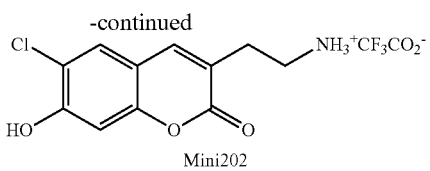

Mini202

(g) BnBr, NaI, NaHCO$_3$, MeCN, 80° C., 18 h, 49%;
(h) Boc—GABA—OH, DIC, DMAP, CH$_2$Cl$_2$, RT, 9 h, 90%;
(i) 2,8,9-triisopropyl-2,5,8,9-tetraaza-1-phosphabicyclo[3.3.3]undecane, 3 Å molecular sieves, benzene, 50° C., 2.5 h, 41%;
(j) trifluoroacetic acid, triisopropylsilane, H$_2$O, RT, 2 h; (k) Pd/C, EtOH/MeOH, RT, 2 h, 73% for two steps;
(l) SO$_2$Cl$_2$, Et$_2$O, 0° C., → RT, 30 min, 47%; (m) BnBr, NaI, NaHCO$_3$, MeCN, 80° C., 16 h, 58%;
(n) Boc—GABA—OH, DIC, DMAP, CH$_2$Cl$_2$, RT, 2.5 h, 81%;
(o) 2,8,9-triisopropyl-2,5,8,9-tetraaza-1-phosphabicyclo[3.3.3]undecane, 3 Å molecular sieves, benzene, 50° C., 17 h, 44%;
(p) trifluoroacetic acid, triisopropylsilane, H$_2$O, 85° C., 16 h, 66%.

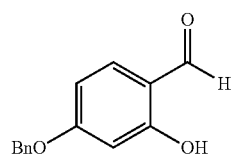

3

To 2,4-dihydroxybenzaldehyde (2.0 g, 14 mmol), NaI (1.0 g, 7.2 mmol), and NaHCO$_3$ (1.5 g, 17 mmol) in acetonitrile (30 mL, 0.50 M) was added benzyl bromide (1.7 mL, 14 mmol). The reaction mixture was stirred at 80° C. for 18 h under argon, cooled to RT, diluted with EtOAc (100 mL), washed with H$_2$O and brine, and dried over MgSO4, and filtered. The filterate was concentrated and purified by flash chromatography (silica, EtOAc:hexanes=1:8) to provided compound 3 as a white solid (49%). $^1$H NMR (CDCl$_3$, 300 MHz): δ 11.48 (1H, s), 9.72 (1H, s), 7.51-7.32 (6H, m), 6.62 (1H, dd, J=8.7, 2.3 Hz), 6.54 (1H, d, J=2.3 Hz), 5.11 (2H, s). $^{13}$C NMR (CDCl$_3$, 100 MHz): δ 194.5, 166.0, 164.6, 135.8, 135.4, 128.9, 128.5, 127.6, 115.5, 109.0, 101.8, 70.5. LRMS (APCI+): Calc'd for C$_{14}$H$_{12}$O$_3$ 228.1 m/z, measured 229.2 (MH+).

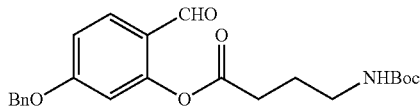

4

To Boc-GABA-OH (0.85 g, 4.2 mmol, 1.2 equiv.) in dichloromethane (35 mL, 0.1 M) were added N,N'-diisopropylcarbodiimide (DIC, 0.70 mL, 4.6 mmol, 1.3 equiv.), 4-(dimethylamino)pyridine (DMAP, 0.11 g, 0.90 mmol, 0.25 equiv.), and compound 3 (0.80 g, 3.5 mmol, 1.0 equiv.) successively. The reaction mixture was stirred at RT for 9 h, after which time the reaction mixture was washed with H$_2$O and brine, dried over MgSO$_4$, filtered, and concentrated. The crude product was purified by flash chromatography (silica, EtOAc:hexanes=1:5→1:3) to give compound 4 as a white solid (90%). $^1$H NMR (CDCl$_3$, 400 MHz): δ 9.91 (1H, s), 7.79 (1H, d, J=8.7 Hz), 7.54-7.30 (5H, m), 6.96 (1H, dd, J=8.6, 2.4 Hz), 6.79 (1H, d, J=2.3 Hz), 5.13 (2H, s), 4.79 (1H, s), 3.36-3.15 (2H, m), 2.71 (2H, t, J=7.2 Hz), 2.02-1.89 (2H, m), 1.45 (9H, s). $^{13}$C NMR (CDCl$_3$, 100 MHz): δ 187.8, 171.5, 164.4, 156.2, 153.1, 135.6, 133.8, 122.0, 113.0, 109.9, 79.4, 70.7, 39.7, 31.2, 28.5, 25.1.

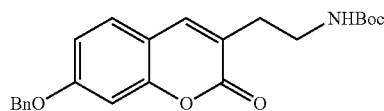

5

To a solution of compound 4 (0.90 g, 2.2 mmol, 1.0 equiv.) in dry benzene (2.0 mL) was added 3 Å molecular sieves (powder, 2.0 g). To this solution, 2,8,9-triisopropyl-2,5,8,9-tetraaza-1-phosphabicyclo[3.3.3]undecane (0.29 g, 0.96 mmol, 0.44 equiv.) in dry benzene (2.0 mL) was added via syringe at 40° C. After being stirred at 50° C. under argon for 2.5 h, the reaction mixture was cooled to RT and loaded directly onto a silica gel column. Purification by flash column chromatography (silica, EtOAc:hexanes=1:3→1:2) yielded compound 5 as a white solid (41%). $^1$H NMR (CDCl$_3$, 400 MHz): δ 7.45-7.27 (7H, m), 6.87 (1H, dd, J=8.6, 2.4 Hz), 6.81 (1H, d, J=2.4 Hz), 5.06 (3H, s), 3.41-3.37 (2H, m), 2.70 (2H, t, J=5.2 Hz), 1.39 (9H, s). $^{13}$C NMR (CDCl$_3$, 100 MHz): δ 162.5, 161.5, 156.4, 155.3, 140.7, 136.3, 129.1, 128.9, 128.7, 127.9, 123.5, 113.6, 113.5, 101.9, 79.5, 70.8, 39.6, 31.9, 28.8. LRMS (APCI+): Calc'd for C$_{23}$H$_{25}$NO$_5$ 395.2 m/z, measured 396.3 (MH+).

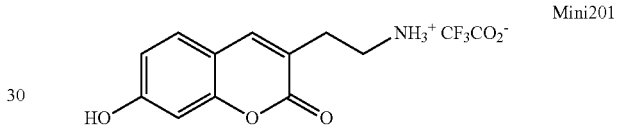

Mini201

Compound 5 (0.36 g, 0.88 mmol) was treated with trifluoroacetic acid (5 mL), triisopropylsilane (0.15 mL), and H$_2$O (0.15 mL) at RT for 2 h, after which time the solvent was removed under reduced pressure and Et$_2$O was added to precipitate the Boc-deprotected compound as a white solid. After filtration, the residue was dried under high vacuum, dissolved in EtOH/MeOH (10 mL/10 mL), and treated with Pd/C (25 mg). After being stirred vigorously under H$_2$ (50 psi) at RT for 2 h using Parr hydrogenation apparatus, the reaction solution was filtered through celite, concentrated, and purified by PR-HPLC using an appropriate linear gradient of acetonitrile containing 10% de-ionized water (A) and 0.1% (v/v) TFA/H$_2$O (B) (3-25% A over 30 min. followed by a steep gradient to 100% A and equilibrium back to 3% A). The fractions containing the product (retention time ~16.9 min) were collected, concentrated, and lyophilized to give Mini201 as a white solid (73% for two steps). $^1$H NMR (DMSO-d6, 400 MHz): δ 7.89 (3H, s), 7.79 (1H, s), 7.47 (1H, d, J=8.5 Hz), 6.80 (1H, dd, J=8.5, 2.3 Hz), 6.73 (1H, d, J=2.2 Hz), 3.10-3.05 (2H, m), 2.72 (2H, t, J=7.0 Hz). $^{13}$C NMR (DMSO-d6, 75 MHz): δ 161.3, 160.9, 154.8, 141.9, 129.2, 119.2, 113.2, 111.6, 101.9, 37.3, 28.6. LRMS (APCI+): Calc'd for C$_{11}$H$_{11}$NO$_3$ 205.6 m/z, measured 206.1 (MH+).

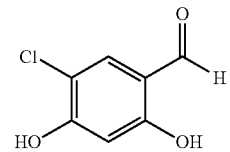

6

To a solution of 2,4-dihydroxybenzaldehyde (3.0 g, 22 mmol) in Et2O (100 mL, 0.22 M) was added dropwise sulfurylchloride (2.1 mL, 26 mmol) at 0° C. under argon. After being stirred at RT for 30 min, the reaction solution was poured into ice-chilled brine, washed with H₂O and brine, dried over MgSO4, filtered, and concentrated. Purification by flash chromatography (Et2O:hexanes=1:2) provided compound 6 as an ivory solid (47%). ¹H NMR (DMSO-d6, 300 MHz): δ 11.38 (1H, s), 10.87 (1H, s), 9.97 (1H, s), 7.59 (1H, s), 6.58 (1H, s). LRMS (APCI+): Calc'd for C₇H₅ClOC3 172.0 ink, measured 173.1 (MH+).

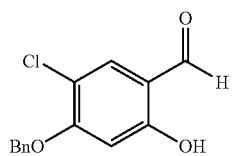

7

To a suspension of compound 6 (0.65 g, 3.7 mmol, 1.0 equiv.), NaI (0.28 g, 1.9 mmol, 0.50 mmol), and NaHCO₃ (0.37 g, 4.4 mmol, 1.2 equiv.) in MeCN (40 mL, 0.1 M) was added benzyl bromide (0.45 mL, 3.7 mmol, 1.0 equiv.) at RT under argon. The reaction solution was stirred at 80° C. under argon for 16 h, cooled to RT, diluted with EtOAc, washed with H₂O and brine, dried over MgSO₄, filtered, and concentrated. Purification by flash chromatography (silica, EtOAc:hexanes=1:10) provided compound 7 as a white solid (58%). ¹H NMR (DMSO-d6, 300 MHz): δ 11.13 (1H, s), 10.02 (1H, s), 7.70 (1H, s), 7.49-7.34 (5H, m), 6.77 (1H, s), 5.27 (2H, s). LRMS (APCI+): Calc'd for C₁₄H₁₁ClO₃ 262.0 m/z, measured 263.1 (MH+).

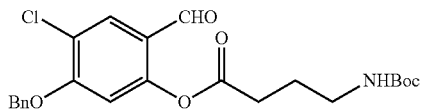

8

To a solution of compound 7 (2.4 g, 9.1 mmol, 1.0 equiv.), 4-(dimethylamino)pyridine (DMAP, 0.29 g, 2.6 mmol, 0.25 equiv.), and Boc-GABA-OH (2.2 g, 11 mmol, 1.2 equiv.) in dichloromethane (100 mL, 0.09 M) was added N,N'-diisopropylcarbodiimide (DIC, 1.8 mL, 12 mmol, 1.3 equiv.) at RT under argon. The reaction mixture was stirred at RT for 1.5 h, washed with H₂O and brine, dried over MgSO₄, filtered, and concentrated. Purification by flash chromatography (silica, EtOAc:hexanes=1:3) provided compound 8 as a white solid (81%). ¹H NMR (DMSO-d₆, 300 MHz): δ 9.90 (1H, s), 7.96 (1H, s), 7.50-7.37 (5H, m), 7.32 (1H, s), 6.95 (1H, t, J=5.4 Hz), 5.30 (2H, s), 3.07-3.00 (2H, m), 2.68 (2H, t, J=7.3 Hz), 1.81-1.72 (2H, m). LRMS (APCI+): Calc'd for C₂₃H₂₆ClNO₆ 447.1 m/z, measured 448.3 (MH+).

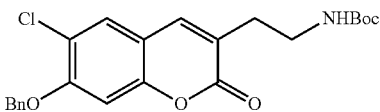

9

To a suspension of compound 8 (1.6 g, 3.6 mmol) and 3 Å molecular sieves (powder, 3.0 g) in dry benzene (15 mL) was added 2,8,9-triisopropyl-2,5,8,9-tetraaza-1-phosphabicyclo[3.3.3]undecane (0.43 g, 1.4 mmol) in dry benzene (15 mL) via syringe at 40° C. under argon. After being stirred at 50° C. for 17 h, the reaction mixture was diluted with CH₂Cl₂ (100 mL), filtered through celite, and concentrated to give a yellow solid. Purification by flash chromatography (silica, EtOAc: hexanes=1:4→1:3) provided compound 9 as an ivory solid (44%). ¹H NMR (CDCl₃, 300 MHz): δ 7.46-7.28 (7H, m), 6.84 (1H, s), 5.17 (2H, s), 4.91 (1H, s), 3.42-3.36 (2H, m), 2.70 (2H, t, J=5.7 Hz), 1.39 (9H, s). ¹³C NMR (CDCl₃, 75 MHz): δ 156.0, 153.1, 139.2, 135.3, 128.8, 128.4, 127.7, 127.2, 127.1, 124.4, 119.6, 113.4, 101.6, 79.3, 71.1, 39.1, 31.6, 28.4. LRMS (APCI+): Calc'd for C₂₃H₂₄ClNO₅ 429.1 m/z, measured 430.8 (MH+).

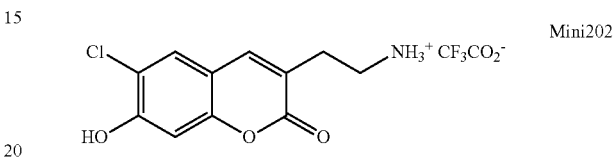

Mini202

To compound 9 (0.28 g, 0.65 mmol, 1.0 equiv.) were added trifluoroacetic acid (3.0 mL), H₂O (0.15 mL), and triisopropylsilane (0.15 mL). The reaction solution was refluxed at 85° C. under argon for 16 h. After cooling to RT, Et₂O (40 mL) was added to the reaction solution to precipitate the crude product as a white solid. The emulsion was centrifuged (4° C., 3000 rpm, 5 min.), and ether was decanted. The crude solid was dried under high vacuum before being dissolved in H₂O/MeOH (4 mL/8 mL) and purified by RP-HPLC using an appropriate linear gradient of methanol (A) and 0.1% (v/v) TFA/H₂O (B) (3-100% A over 25 min. followed by an equilibrium back to 3% A). The fractions containing the product (retention time ~16.2 min) were collected, concentrated, and lyophilized to give Mini202 as a white solid (66% for two steps). ¹H NMR (DMSO-d6, 300 MHz): δ 11.39 (1H, s), 7.76-7.72 (5H, m), 6.92 (1H, s), 3.06 (2H, t, J=7.2 Hz), 2.72 (2H, t, J=6.9 Hz), ¹³C NMR (CD₃OD, 75 MHz): δ 163.4, 157.8, 154.9, 142.8, 129.6, 122.0, 119.4, 114.0, 104.3, 39.4, 30.2. LRMS (APCI+): Calc'd for C₁₁H₁₀ClNO₃ 239.0 m/z, measured 240.3 (MH+).

Scheme S4. Synthesis of Mini301, 302, and 401.

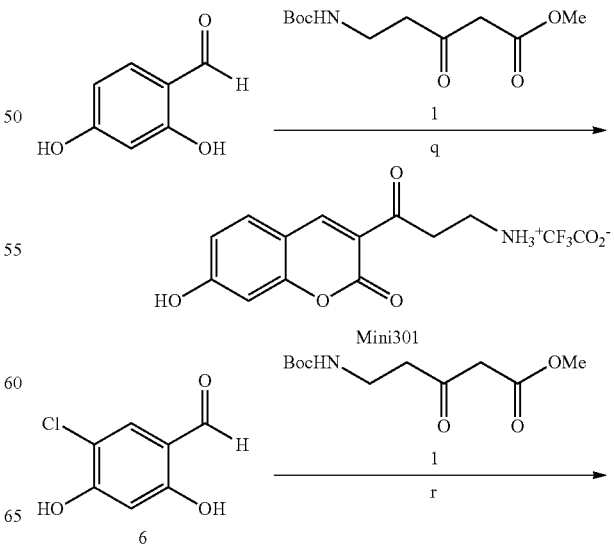

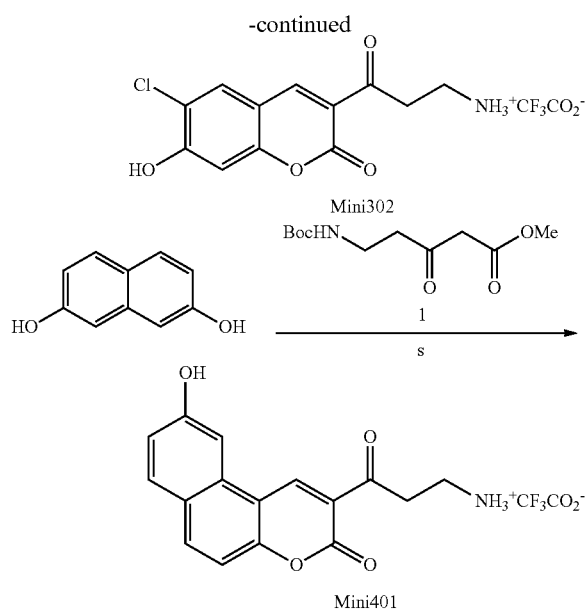

(q) Methanesulfonic acid (MSA), RT, 1.5 h, 56%;
(r) MSA, RT, 2.5 h, 20%;
(s) MSA, RT, 4 h, 5%.

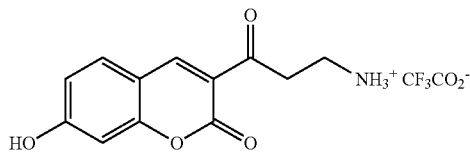

Mini301

To a mixture of 2,4-dihroxybenzaldehyde 6 (50 mg, 0.36 mmol) and 1 (59 mg, 0.24 mmol) was added methanesulfonic acid (1.0 mL) at 0° C. The clear brown solution gradually became dark orange within 1.5 h after which time the reaction mixture was diluted with cold (−30° C.) ethyl ether (10 mL), and the crude mixture was extracted into H2O (3 mL) and purified by RP-HPLC using an appropriate linear gradient of acetonitrile containing 10% de-ionized water (A) and 0.1% (v/v) TFA/H$_2$O (B) (3-50% A over 20 min. followed by a steep gradient to 100% A and equilibrium back to 3% A). The fractions containing the product were collected, concentrated, and lyophilized to give Mini301 as a white solid (56%). $^1$H NMR (DMSO-d6, 300 MHz): δ 11.37 (1H, s), 8.68 (1H, s), 7.85 (1H, d, J=8.6 Hz), 7.75 (3H, bs), 6.89 (1H, dd, J=8.6, 2.2 Hz), 6.79 (1H, d, J=2.1 Hz), 3.38 (2H, t, J=6.8 Hz), 3.14-3.10 (2H, m). $^{13}$C NMR (DMSO-d6, 75 MHz): δ 194.3, 164.8, 159.3, 157.5, 148.7, 133.1, 118.2, 114.6, 110.9, 102.0, 34.3. LRMS (APCI+): Calc'd for C$_{12}$H$_{11}$NO$_4$ 233.1 m/z, measured 234.1 (MH+).

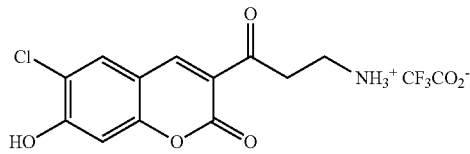

Mini302

To a mixture of 5-chloro-2,4-dihydroxybenzaldehyde (40 mg, 0.18 mmol) and 1 (29 mg, 0.12 mmol) was added methanesulfonic acid (1.0 mL) at 0° C. The clear brown solution gradually became dark orange within 2.5 h after which time the reaction mixture was diluted with cold (−30° C.) ethyl ether (10 mL), and the crude mixture was extracted into H$_2$O (3 mL) and purified by RP-HPLC using an appropriate linear gradient of acetonitrile containing 10% de-ionized water (A) and 0.1% (v/v) TFA/H$_2$O (B) (3-50% A over 20 min. followed by a steep gradient to 100% A and equilibrium back to 3% A). The fractions containing the product were collected, concentrated, and lyophilized to give Mini302 as a yellow solid (20%). $^1$H NMR (DMSO-d6, 400 MHz): δ 8.65 (1H, s), 8.11 (1H, s), 7.75 (3H, bs), 6.95 (1H, s), 3.38 (2H, t, J=6.7 Hz), 3.14-3.07 (2H, m). $^{13}$C NMR (CD$_3$OD, 75 MHz): δ 195.6, 161.3, 160.9, 157.5, 149.3, 132.6, 120.7, 120.5, 113.1, 104.0, 40.4, 35.9. LRMS (APCI+): Calc'd for C$_{12}$H$_{10}$ClNO$_4$ 267.0 m/z, measured 268.2 (MH+).

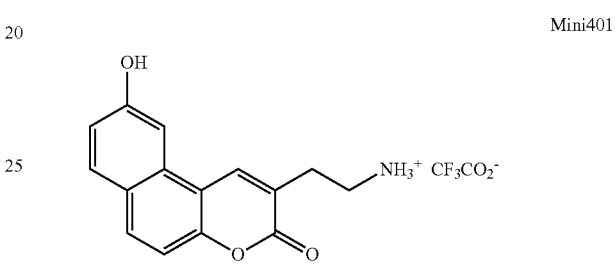

Mini401

To a mixture of 2,7-dihydroxynaphthalene (0.20 g, 1.3 mmol) and 1 (0.20 mg, 0.83 mmol) was added methanesulfonic acid (1.3 mL, 21 mmol) at 0° C. The clear brown solution gradually became dark orange within 4 h after which time the reaction mixture was diluted with cold (−30° C.) ethyl ether (10 mL), centrifuged (3000 rpm) at 4° C. for 20 minutes. After removing the ether by aspiration, the residual orange solid was dried under high vacuum, dissolved in H$_2$O (3 mL), and purified by RP-HPLC using an appropriate linear gradient of acetonitrile containing 10% de-ionized water (A) and 0.1% (v/v) TFA/H$_2$O (B) (3-50% A over 20 min. followed by a steep gradient to 100% A and equilibrium back to 3% A). The fractions containing the product were collected, concentrated, and lyophilized to give Mini401 as a white solid (5%). $^1$H NMR (DMSO-d6, 400 MHz): δ 10.21 (1H, s), 8.08 (1H, d, J=8.9 Hz), 7.94 (1H, d, J=8.8 Hz), 7.84 (3H, bs), 7.72 (1H, s), 7.33 (1H, d, J=8.8 Hz), 7.18 (1H, dd, J=8.8, 2.0 Hz), 6.44 (1H, s), 3.54 (2H, t, J=6.8 Hz), 3.32-3.29 (2H, m). $^{13}$C NMR (DMSO-d6, 75 MHz): δ 159.2, 157.6, 155.1, 153.0, 133.9, 131.5, 130.8, 125.3, 117.0, 115.2, 114.0, 111.9, 1079, 37.2, 33.9. LRMS (APCI+): Calc'd for C$_{15}$H$_{13}$NO$_3$ 255.1 m/z, measured 256.2 (MH+).

Example 2

HPLC Analysis of Coumarin Probes

Figure 3:
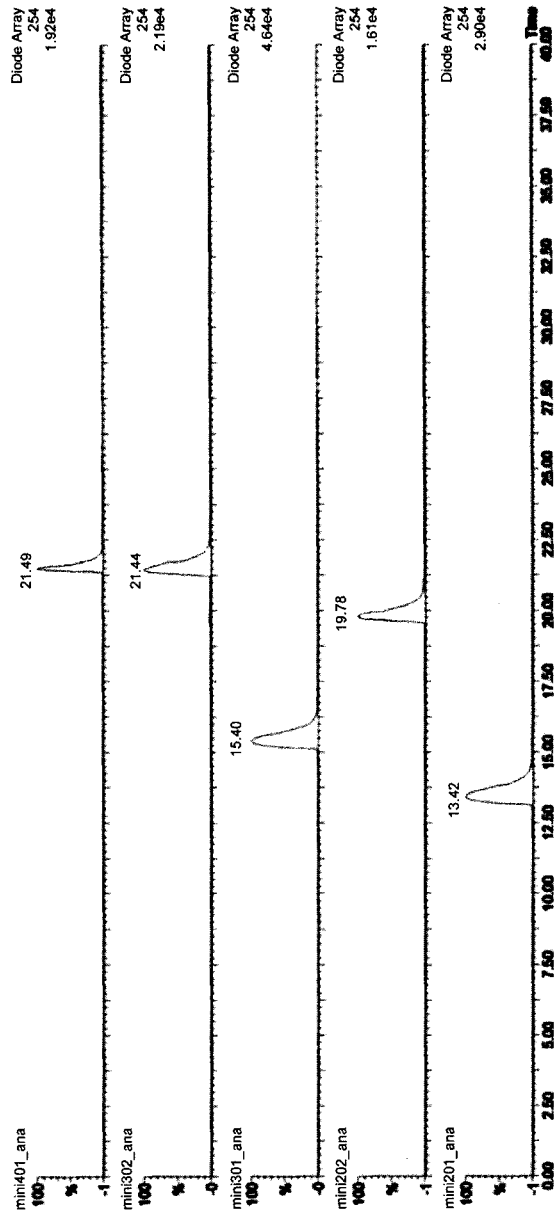
FIGS. 3-4. RP-HPLC chromatograms of probes (absorption detection at 254 nm).
Figure 4:
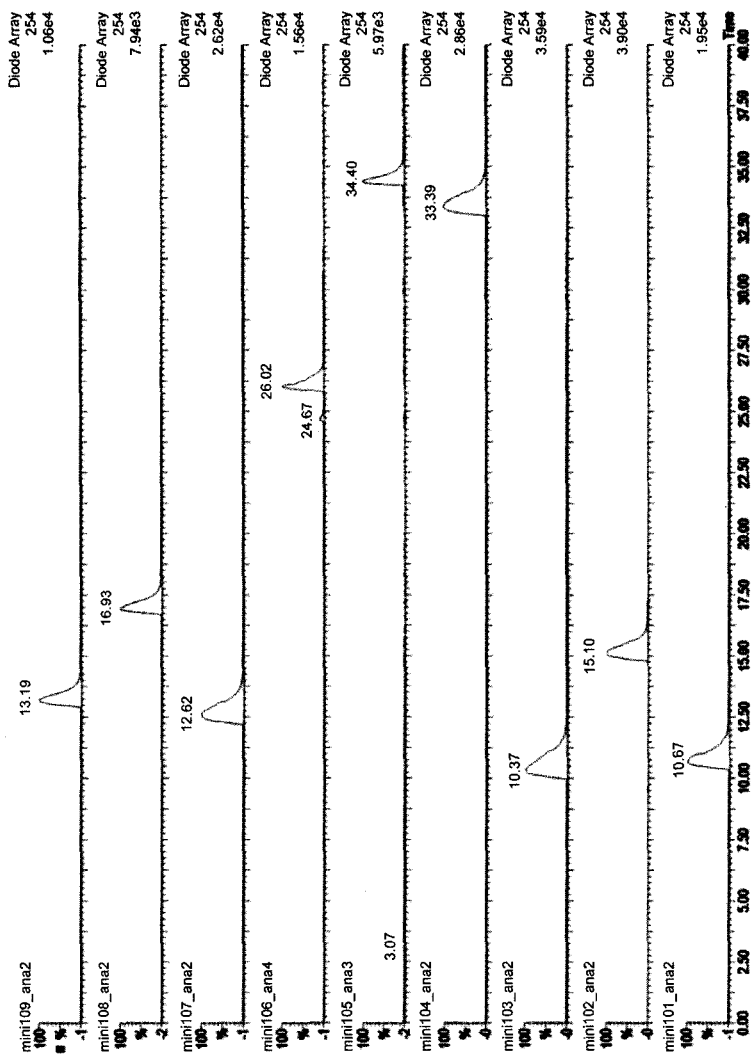

As an estimate of the compounds' purity, all the synthetic probes were analyzed by analytical reverse phase HPLC (column is from GRACE VyDAC protein&peptide C18, cat. #218TP54) using an appropriate linear gradient of acetonitrile containing 10% deionized water (A) and 0.1% (v/v) TFA/H$_2$O (B). (for Mini101~104, 107~409, 201~302: 3-30% A over 40 min. followed by equilibrium back to 3% A; for Mini105, 106, 401: 3-50% A over 40 min. followed by equilibrium back to 3% A). (See FIGS. 3 and 4)

Example 3

Photophysical Characterization and Measurement of log D Values

General

Ultraviolet absorption spectra were measured on a Molecular Devices SPECTRAmax Plus 384 UV-Visible spectrophotometer operated through a Dell Pentium PC by SOFTmax software. Fluorescence measurements (emission/excitation) were carried out on a Jobin Yvon Fluorolog fluorescence spectrofluorometer.

Absorption

UV absorption spectra were taken by adding probe (2 μL of 10 mM stock solution in DMSO) to 998 μL of PBS buffer at different pH values (final probe conc.=20 μM) in quartz cuvette.

Emission/Excitation

Excitation/Emission spectra were taken by adding probe (20 μL of 0.1 mM stock solution in distilled water) to 980 μL of PBS buffer of different pH values (final probe conc.=2 μM) in quartz cuvette.

pKa

The pKa values of probes were determined from the absorption spectra. The absorbance at $\lambda_{abs,\ max}$ was plotted versus pH of the PBS solution; the data were fit to a sigmoid curve using KaleidaGraph (Synergy Software, Reading, Pa.) nonlinear regression analysis program to determine the pKa value.

log D

The log D values were determined by traditional shake flask method. Each measurement was performed in duplicate as follows. First, 20 μM probe solution in 1 mL PBS (pH 7.4) was prepared to which 1 mL of n-octanol was added and mixed thoroughly. The mixture was kept in dark for 3 days for complete equilibrium, and the concentrations of probe in each layer were determined based on the UV absorbance. Log D values were determined based on the equation; $\log D = \log [\text{probe}]_{oct} - \log [\text{probe}]_{PBS}$, where $[\text{probe}]_{oct}$ and $[\text{probe}]_{PBS}$ are the concentrations of the probe in n-octanol and PBS, respectively.

TABLE 1

Summary of photophysical properties, logD, and pKa values.

| Compound | λabs, max | λem, max | λex, max | LogD (at pH 7.4) | pKa |
|---|---|---|---|---|---|
| Mini101 | 324, 365 | 460 | 333, 368 | −0.94 | 7.24 |
| Mini102 | 330, 372 | 456 | 341, 373 | −1.45 | 5.77 |
| Mini103 | 328, 370 | 453 | 333, 371 | −1.98 | 5.95 |
| Mini104 | 333, 382 | 471 | 341, 400 | 0.89 | 7.94 |
| Mini105 | 338, 390 | 474 | 343, 412 | 1.3 | 8.49 |
| Mini106 | 330, 378 | 465 | 337, 378 | 0.18 | 6.09 |
| Mini107 | 325, 363 | 460 | 334, 371 | 0.28 | 7.30 |
| Mini108 | 332, 372 | 459 | 341, 373 | −0.26 | 5.63 |
| Mini109 | 329, 369 | 453 | 338, 372 | −0.73 | 5.88 |
| Mini201 | 325, 363 | 463 | 334, 373 | −1.01 | 7.60 |
| Mini202 | 330, 370 | 460 | 335, 370 | −1.42 | 6.06 |
| Mini301 | 363, 418 | 458 | 373, 420 | 0.14 | 7.00 |
| Mini302 | 365, 422 | 463 | 420 | 0.24 | 4.68 |
| Mini401 | 352, 410 | — | — | 0.86 | 9.36 |

Example 4

Protocols for Fluorescent Microscopy Assay in VMAT2/HEK Cells and Assay Result Summary HEK GNTI⁻ (nonglycosylating) cell line stably expressing VMAT2 (VMAT2-HEK) and HEK GNU⁻ cell line stably transected with TetR (HEK) to serve as a control were kindly provided by the laboratory of Robert Edwards at UCSF. Cells were grown in DMEM+Glutamax (Invitrogen #10569) with 10% fetal bovine serum (FBS) (Atlanta Biologicals), 100 U/ml penicillin (Nitrogen), and 100 μg/ml streptomycin (Invitrogen). For fluorescent microscopy experiments, cells were plated on poly-D-lysine (Sigma Aldrich, conc.=0.1 mg/mL) coated six-well dishes at a density of 1.0×105 cells per well and grown at 37° C. in 5% CO2. After 5 days, the cells looked fibroblastic and had reached ~70% confluence. The medium was removed by aspiration, and the cells were washed with PBS (2 mL per well). To investigate the inhibitory effect of tetrabenazine (TBZ) and reserpine, cells were incubated in 1 mL of experimental media (DMEM minus phenol red (Invitrogen) with 4 mM L-glutamine (Invitrogen) and 1% charcol/dextran-treated FBS (Atlanta Biologicals)) containing inhibitor (1 μM or 0 μM as a control, prepared from 10 mM stock solution in DMSO) at 37° C. in 5% CO2 for 1 hour. Then, the probe uptake was initiated by adding 0.1 mL of experimental media containing probe (220 μM, prepared from 10 mM stock solution in DMSO, final conc.=20 μM in the uptake assay). After incubating at 37° C. for 30 minutes, the media was removed by aspiration, and the cells were washed with PBS (2 mL per well) and treated with probe-free experimental media. Fluorescence images were taken by using Leica FW 4000 equipped with Chroma custom filter cube (ex=350/50 nm, em=460/50 nm) and Hamamatsu digital camera C4742-95. The fluorescent images and bright field images were acquired for 2000 ms and 37 ms, respectively. All images were adjusted using the same contrast and brightness level using Images J (National Institute of Health).

For the chloroquine-induced Mini202 redistribution experiment, after probe loading and cell washing with PBS, 1 mL of experimental media containing 300 μM chloroquine was added to the cells at RT for 3 minutes, after which time fluorescent images were taken by the same procedure described above.

Figure 5:
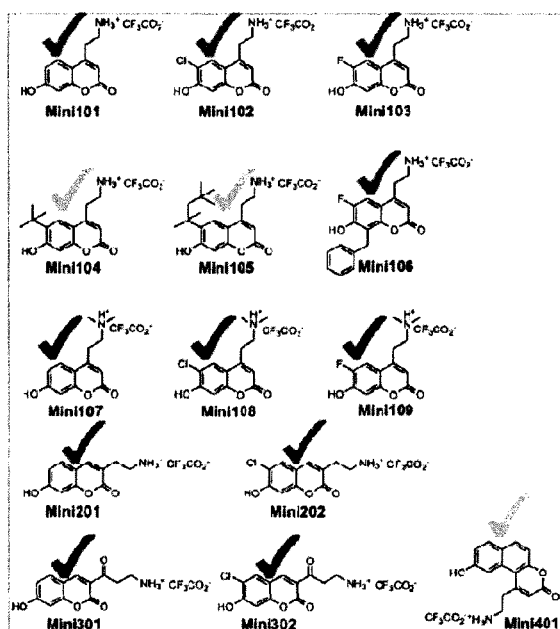
FIG. 5. Summary of results from screening of Mini probes using VMAT2/HEK or HEK cells. Six probes exhibited VMAT2-dependent uptake affording fluorescent puncta, i.e., they were taken up by VMAT2/HEK cells but not control HEK cells and the uptake in VMAT2/HEK cells was abolished by VMAT inhibitors tetrabenazine (TBZ) and reserpine (red sign). Three probes were taken up as fluorescent puncta by both of VMAT2/HEK cells and HEK cells, regardless of the presence/absence of tetrabenazine or reserpine (yellow sign). Five probes showed no uptake by either VMAT/HEK or HEK cells (black sign).

The results (FIG. 5) indicated that probes Mini101-103, Mini106, Mini201, and Mini202 are VMAT2 substrates. They are too polar to be taken up by HEK cells that lack VMAT2, while in VMAT2/HEK cells the VMAT2-mediated transport to acidic organelles also drives the passive diffusion across the plasma membrane. Compounds that are relatively lipophilic show non-selective uptake (e.g. Mini104, 105, and 401).

More polar compounds that are not VMAT substrates show no uptake in either cell lines (Mini107-109, Mini301 and 302).

Example 5

Protocols or Fluorescent Microscopy in PC-12 Cells

PC-12 cells were purchased and maintained according to the protocols provided by American Type Culture Collection (ATCC, CRL-1721). Among the two variations of PC-12 provided by ATCC, the one displaying loosely adherent (with no PDL coating) and multicell-aggregating phenotype was used. PC-12 cells were grown in RPMI-1640 (Invitrogen, #11875) with 10% horse serum (Invitrogen, #16050-114), 5% fetal bovine serum (FBS) (Atlanta Biologicals), 100 U/ml penicillin (Invitrogen), and 100 μg/ml streptomycin (Invitrogen). For fluorescent microscopy experiments, cells were plated on poly-D-lysine (Sigma Aldrich, conc.=0.1 mg/mL) coated six-well dishes at a density of 5.0×105 cells per well and grown at 37° C. in 5% CO2. After 6 days when the cells get ~70% confluent, the medium was removed by aspiration, and the cells were washed with PBS (2 mL per well). To investigate the inhibitory effect of reserpine, cells were incubated in 1 mL of experimental media (RPMI-1640 minus phenol red supplemented with 2 mM L-glutamine (Invitrogen #11835), 0.5% charcol/dextran treated FBS (Atlanta Biologicals), 1% charcol/dextran-treated horse serum (Invitrogen), 100 U/ml penicillin (Invitrogen), and 100 µg/ml streptomycin (Invitrogen)) containing reserpine (1 µM prepared from 10 mM stock solution in DMSO) at 37° C. in 5% $CO_2$ for 1 hour. Then, the probe uptake was initiated by adding 0.1 mL of experimental media containing Mini202 (220 µM, prepared from 10 mM stock solution in DMSO, final conc.=20 µM in the uptake assay) to the cells. After incubating the cells at 37° C. for 1 hour, the medium was removed by aspiration, and cells were washed with PBS (2 mL per well) and treated with dye-free experimental media. Fluorescence images were taken by using Leica FW 4000 equipped with Chroma custom filter cube (ex=350/50 nm, em=460/50 nm) and Hamamatsu digital camera C4742-95. The fluorescent images and bright field images were acquired for 2000 ms and 37 ms, respectively. All images were adjusted using the same contrast and brightness level using Images J (National Institute of Health).

Example 6

Protocols for Two-Photon Laser Scanning Confocal Microscopy and pH Measurement of Secretory Vesicles in PC-12 Cells In Situ Calibration Curve PC-12 cells were grown on 35×10 mm tissue culture dish (Becton Dickinson Labware) under the cell maintenance conditions as described above. To calibrate Mini202 fluorescence intensity ratio from 692 nm and 760 nm dual excitations for a range of pH values in situ, vesicles of PC-12 cells were loaded with Mini202 as described, and then the extracellular media for the cells was replaced with a buffer of known pH in the presence of monensin, a Na+/H+ antiporter, and nigericin, a $K^+/H^+$ antiporter, which act to equilibrate the pH of cytosol and vesicles of PC-12 cells with that of extracellular media. The pH calibration solution contains 125 mM KCl, 20 mM NaCl, 0.5 mM CaCl2, 0.5 mM MgCl2, 5 µM nigericin, 5 µM monensin, and 25 mM buffer (acetate for pH 4.27, 4.69, 5.39; MES for pH 5.74, 6.15; HEPES for pH 6.41, 6.95, 7.52). Cells were incubated with 20 µM Mini202 in the experiment medium for 1 hour at 37° C. and washed with dye-free PBS at RT. Then, the cells were treated with 1 mL of calibration solution at known pH for 8~10 minutes at RT before acquiring fluorescent images by two-photon laser confocal microscope (Prairie Ultima multiphoton microscope operated with Prairie View 3.0.0.3 software for scan control and image collection (Prairie Technologies, Middleton, Wis.) with Mai Tai HP Ti:sapphire laser (Spectra-Physics, Newport Instruments, Irvine, Calif.) (excitation 692 or 760 nm/emission 430-510 nm) and water-immersion, IR-corrected objective from Olympus designated LUMPlanFl/IR 60×/0.90 NA on an Olympus BX61W1 microscope). For each 35 mm plate, two sets of fluorescent images by 692 nm or 760 nm excitation were collected, and this process was repeated at least 2-3 times using a new plate of cells. The ratio of fluorescence intensity by excitation at 760 nm and 692 nm (I760/I692) was plotted versus pH of the calibration solution; the data were fit to a sigmoid curve using KaleidaGraph (Synergy Software, Reading, Pa.) nonlinear regression analysis program to construct a calibration curve and determine Mini 202's in situ pKa value (pKa 5.93±0.04, FIG. 6).

Ratiometric pH Measurements of LDCVs in PC-12 Cells In Situ

After PC-12 cells were incubated with 20 µM Mini202 for 1 h at 37° C. in 5% CO2, fluorescent images containing ~10 cells were acquired by dual excitations (692 nm and 760 nm) using Prairie confocal microscope, as described. The brightness level and contrast ratio were equally adjusted for all images by using Images J (National Institute of Health). Mean fluorescence intensity of all puncta from 7-10 cells was determined using Velocity version 4.4 software (Perkin Elmer, Waltham, Mass.), which in turn was used to get fluorescence intensity ratio I760/I692 from at least 50 individual cells.

Figure 6:
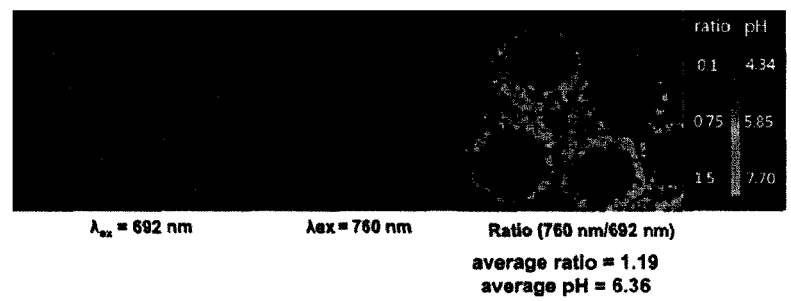
FIG. 6. Two photon laser confocal image of PC-12 cells treated with 100 µM methamphetamine for 5 minutes at RT with two-photon excitation (a) at 692 nm; (b) at 760 nm. (c) Pseudo-color image of I760/I692 and corresponding pH values. The vesicular pH in PC-12 cells increased from 5.9 to 6.4 by the effect of methamphetamine.

In order to measure the pH change induced by methamphetamine, the PC-12 cells preloaded with Mini202 were washed with PBS, treated with 1 mL of experimental media containing 100 methamphetamine (prepared from 50 mM stock solution in DMSO) for 5 minutes at RT, and imaged as described (FIG. 6).

Example 7

Preparation and Uptake Test of the Chloride Salt of Mini202

Figure 7:
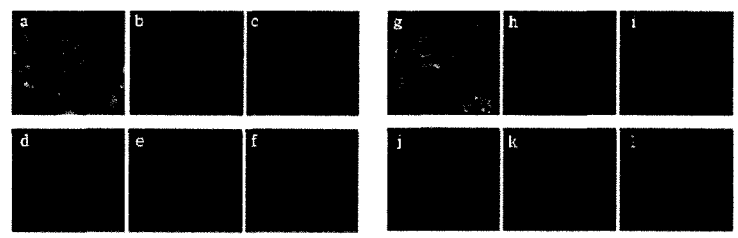
FIG. 7. Uptake study of Mini202.TFA (a~f) and Mini202.HCl (g~l) in VMAT2/HEK cells and HEK cells. 20 µM Mini202.TFA or Mini202.HCl were incubated in VMAT2/HEK cells for 30 minutes to afford fluorescent puncta (a, g), and preincubation of the VMAT2/HEK cells with VMAT2 inhibitor TBZ (b, h) or reserpine (c, i) abolished the uptake of Mini202.TFA and Mini202.HCl. In HEK cells, both of the salt forms of Mini202 showed no uptake in the absence (d, j) and presence of TBZ (e, k) or reserpine (f, l).

In order to avoid possible toxic effects of trifluoroacetic acid present with Mini202 as a salt form, we prepared Mini202 as chloride salt from the corresponding TFA salt as described below. Mini202.TFA (20 mg) was dissolved in mixture of 0.8 M HCl aqueous solution (5 mL) and methanol (0.2 mL). The cloudy solution became clear after heating at 80° C. for 5 minutes. After cooling down to RT, the solution was lyophilized to afford Mini202.HCl as a white solid (12 mg). The purity of the compound was checked by $^1H$ NMR spectroscopy, analytical reverse-phase HPLC, and mass spectroscooy. $^{19}F$ NMR was taken to confirm the absence of TFA in the Mini202.HCl salt. The activity of Mini202.HCl salt toward VMAT2 was tested in VMAT2/HEK and HEK cells was tested by the same method described in Part IV. Both of Mini202.TFA and Mini202.HCl salts showed same pattern of punctuate uptake in a VMAT2-dependent manner, and such uptake was abolished in the presence of VMAT2 inhibitors (1 µM TBZ or 1 µM reserpine), which suggest the salt conversion from TFA to HCl does not affect the Mini202's availability to be a VMAT2 substrate in VMAT2/HEK cells (FIG. 7).

Figure 2:
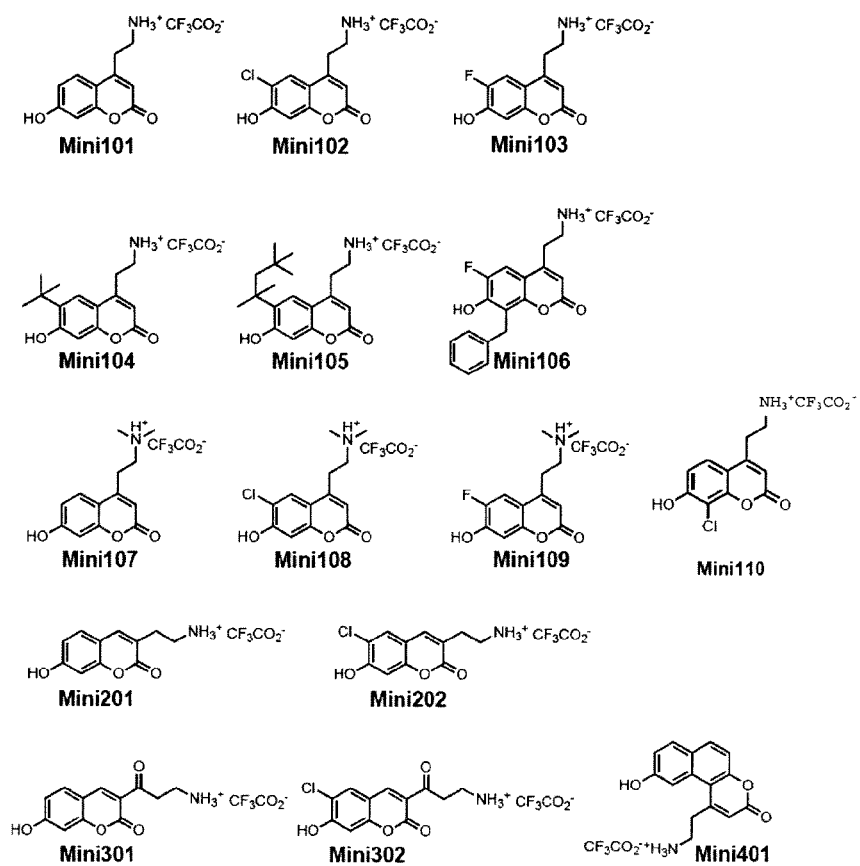
FIG. 2. Structure of coumarin probes as trifluoroacetate salt.

Discussion pH responsive FFNs-VMAT substrates with a built-in ratiometric fluorescent pH sensor were developed. The aminoethyl group was maintained as the key VMAT recognition element. Phenols exhibit pH-dependent photophysical properties, which is related to the equilibrium between the protonated phenol and the deprotonated phenolate forms. Specifically, 7-hydroxycoumarin (umbelliferone, FIG. 8B) exhibits a pH-responsive, ratiometric absorption/excitation profile. [12] Accordingly, probe Mini101 (FIG. 2C) was synthesized and the $pK_a$ value of 7.2 was obtained from the absorption measurements. Since the $pK_a$ of Mini101 is too high for an accurate measurement in the relevant pH range of synaptic or secretory vesicles (5-6), electron-withdrawing groups (Cl and F) were introduced at the 6-position of coumarin to decrease the $pK_a$ of the phenolic hydroxyl group.

Figure 8:
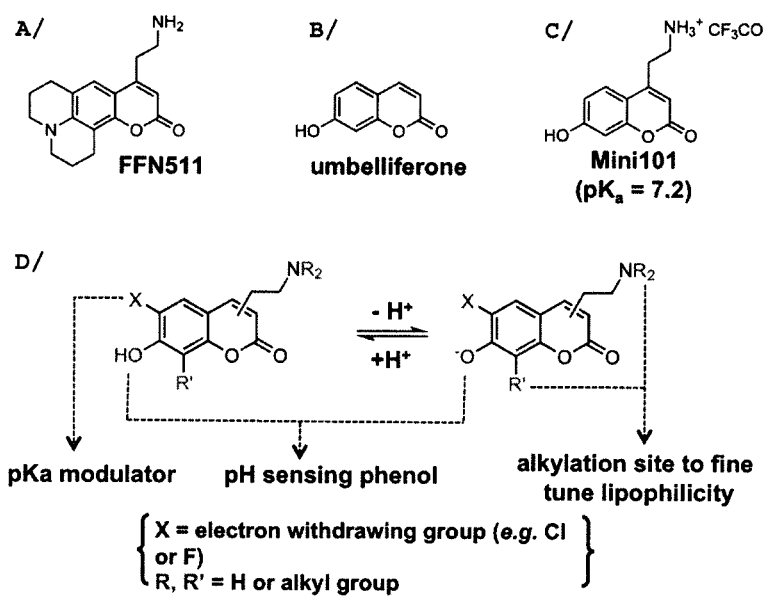
FIG. 8. Design of pH responsive FFNs based on the coumarin nucleus. (A) Structure of FFN511, the first example of FFN probes. (B) Structure of umbelliferone. (C) Chemical structure of Mini101. (D) The key structural elements for optimization of photophysical, physical, and functional properties of pH responsive FFNs.

In addition to the photophysical properties, the lipophilicity of FFNs was examined as an additional key design parameter, affecting membrane permeability by passive diffusion, and ultimately determining the selectivity between VMAT-expressing cells and other cells lacking VMAT. Lipophilicity is fine-tuned by adding alkyl groups either to the coumarin ring (at position C-8) or the amino group (FIG. 8D).

Figure 9:
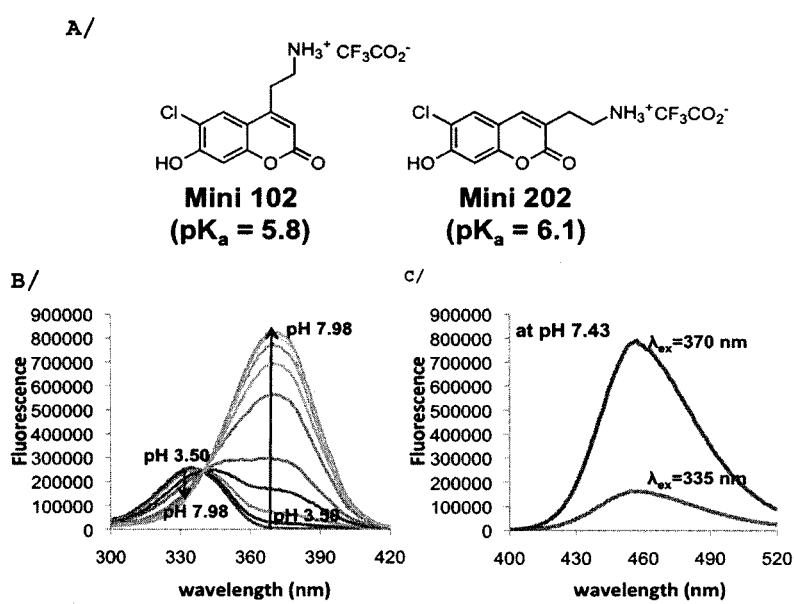
FIG. 9. (A) Structure of Mini102 and Mini202 (B) Excitation spectra of Mini202 ($\lambda_{em}$=458 nm) at different pH values in phosphate buffer. (C) Emission spectra of Mini202 in pH 7.43 phosphate buffer ($\lambda_{ex}$=335 nm and 370 nm, [Mini202]=2 µM).

According to these design directives, a series of 14 compounds was prepared. For all compounds, the photophysical properties, pH responsiveness, and lipophilicity were investigated. Placing the chlorine or fluorine adjacent to the hydroxy group resulted in a large decrease of $pK_a$, as exemplified by probes Mini102 and Mini202 (FIG. 9A, $pK_a$=5.8 and 6.1, respectively). The excitation spectrum of the probe Mini202 is shown in FIG. 9B; it is strongly dependent on pH, exhibiting two fully resolved maxima at 335 nm and 370 nm, where the former corresponds to the protonated phenolic form and the latter to the deprotonated phenolate form. Mini202 is sufficiently fluorescent, and the emission intensity ($\lambda_{max}$=458 nm) is dependent on the excitation wavelength and pH. Therefore, the fluorescence intensity ratio at 458 nm obtained by dual excitation at two different wavelengths gives the pH of the solution. In addition, Mini202 is highly polar (log D=−1.5, obtained by partitioning between pH 7.4 phosphate buffer and n-octanol), which is responsible for slow cell uptake and low background fluorescence.

Figure 10:
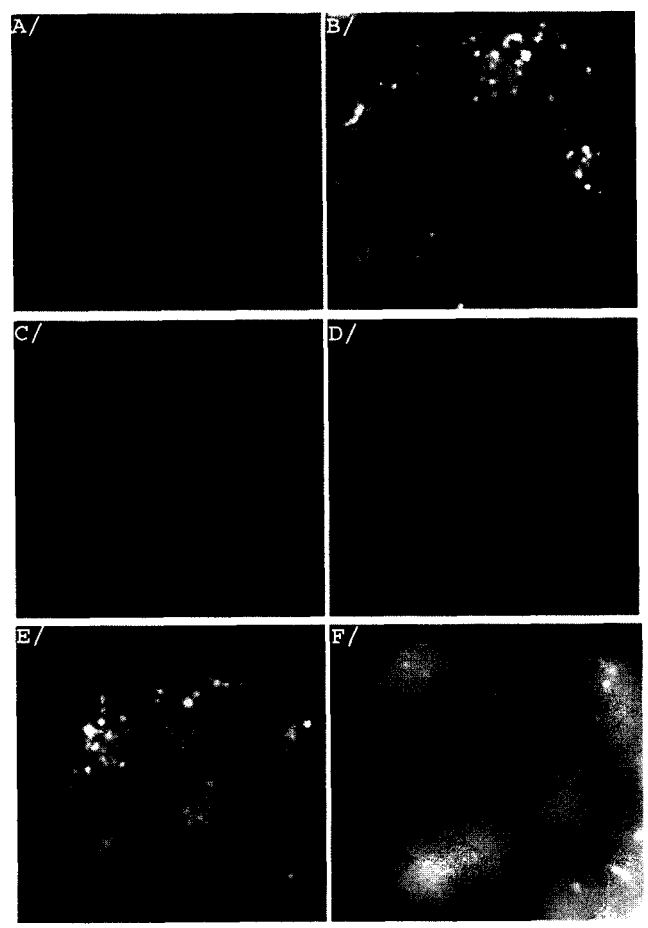
FIG. 10. Fluorescent microscopy images of Mini202 (20 µM, 30 min. incubation) in (A) non-transfected HEK cells, (B) VMAT2-HEK cells, (C) VMAT2-HEK cells pre-incubated with 1 µM TBZ and (D) VMAT2-HEK cells pre-incubated with 1 µM reserpine. (E) VMAT2-HEK cells labeled with Mini202 (3 minutes after rinsing the cells with dye-free media). (F) Addition of the lipophilic base chloroquine (300 µM, 3 min.) led to redistribution of Mini202 from the acidic vesicles to cytosol. $\lambda_{ex}$=350±25 nm, $\lambda_{em}$=460±25 nm.

The compound series was profiled by fluorescent microscopy using human embryonic kidney (HEK) cells stably transfected with VMAT2 (VMAT2-HEK). Six probes showed VMAT2-dependent uptake, Mini202 giving the highest uptake at the selected incubation time (FIG. 10). VMAT2-HEK cells were incubated with Mini202 (final conc.=20 µM) for 30 minutes and imaged by fluorescent microscopy with $\lambda_{ex}$=350±25 nm and $\lambda_{em}$=460±25 nm to afford punctuate fluorescence patterns, consistent with VMAT2 expression in acidic organelles (FIG. 10B). No uptake of Mini202 was observed in non-transfected HEK cells (FIG. 10A), and the uptake of Mini202 was strongly diminished by pre-incubating VMAT2-HEK cells with VMAT2 inhibitors, tetrabenazine (TBZ) or reserpine (FIG. 10C, 10D). These results indicate that selective accumulation of Mini202 in intracellular organelles is mediated by VMAT2. Furthermore, addition of the lipophilic base chloroquine to the VMAT2-HEK cells labeled with Mini202 resulted in diffusion of the punctuate fluorescence pattern, which is consistent with redistribution of the probes from the vesicles to the cytoplasm caused by collapsing the pH gradient (FIG. 10F).

Figure 11:
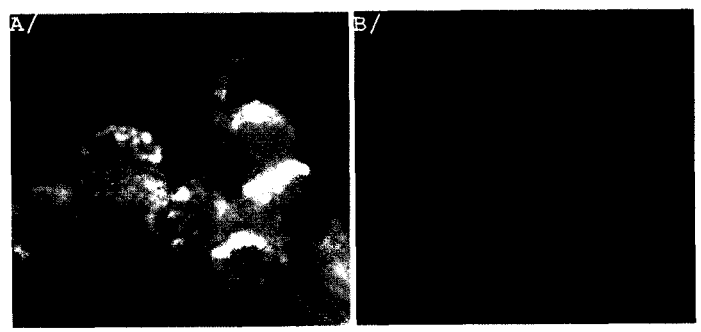
FIG. 11. (A) PC-12 cells incubated with 20 µM Mini202 for 1 h. (B) PC-12 cells pre-incubated with VMAT1 inhibitor reserpine (1 µM, 1 h) followed by 20 µM Mini202 treatment for 1 h. The uptake of Mini202 is completely inhibited by reserpine.

The uptake of Mini202 in PC-12 cells, a cell line derived from a rat pheochromocytoma which is widely used as a model of chromaffin cells and neuronal presynaptic terminals [4] was tested. PC-12 cells express mostly VMAT1 on their secretory large dense core vesicles (LDCVs) where catecholamines accumulate (mostly dopamine and norepinephrine). PC12 cells were incubated with Mini202 (20 µM) for 1 h and imaged to give fluorescent puncta consistent with the distribution of LDCVs (FIG. 11A). Pre-incubation of PC-12 cells with VMAT1 inhibitor reserpine (1 µM) resulted in no detectable labeling by Mini202 (FIG. 11B), indicating that Mini202 labels LDCVs, and that Mini202 is a VMAT1 substrate.

Figure 12:
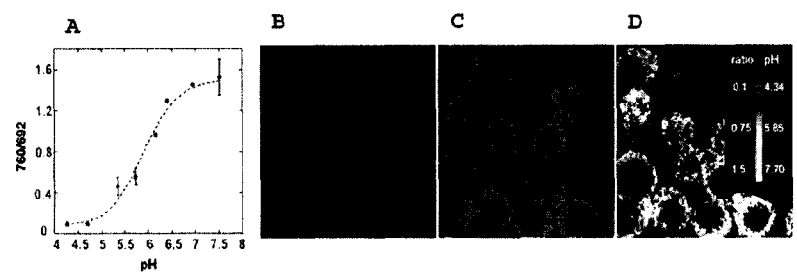
FIG. 12. Measuring pH of catecholamine secretory vesicles in PC12 cells with Mini202 via two-photon fluorescence microscopy. (A) In situ calibration curve of fluorescence intensity ratio from 760 nm irradiation and 692 nm irradiation ($\lambda_{em}$=470±30 nm, p$K_a$=5.93±0.04, n=3) in PC-12 cells as a function of vesicle pH. (B) Two-photon image of PC-12 cells incubated with 20 µM Mini202 for 1 h at $\lambda_{ex}$=760 nm and (C) $\lambda_{ex}$=692 nm. (D) Pseudo-color image of I$_{760}$/I$_{692}$ and corresponding pH values.

Finally, in situ pH measurement of LDCVs in PC-12 cells using a two-photon fluorescence microscope was examined. An in situ calibration curve was generated by dual excitation (760 and 692 nm) ratiometric imaging of Mini202 in PC-12 cells, incubated in a series of buffers of known pH in the presence of 5 µM ionophore nigericin and monensin, which act to equilibrate the vesicular pH with the surrounding media (FIG. 12A). [14] Using this calibration curve, the mean pH of LDCVs in PC-12 cells was determined to be 5.88±0.08 by extrapolating the ratio (0.75±0.08) of the two fluorescence intensities from the vesicles after excitation at 760 nm (FIG. 12B) and 692 nm (FIG. 12C). Although pH of secretory vesicles has not previously been measured in PC12 cells, this value is in general agreement with measurements in related cells via in situ and other methods (5.4 in primary chromaffin cells [9], 5.5 in AtT-20 cells [7], 5.6-5.7 in synaptic vesicles of hippocampal and dopaminergic neuronal culture [6]).

Furthermore, a pharmacological manipulation of vesicular acidity was quantitatively examined. It has previously been reported that acute exposure of chromaffin cells to methamphetamine rapidly diminishes the pH gradient. [9, 15] When PC-12 cells loaded with Mini202 were exposed to 100 µM methamphetamine for 5 minutes, the emission ratio increased to 1.19, which corresponds to pH 6.36. This result is consistent with the proposed pharmacological mode of action of methamphetamine as a transmitter releaser, which relies on redistribution on the vesicular content to the cytoplasm caused by decreasing the pH gradient.

In summary, two molecular functions—the transport by VMAT and ratiometric optical pH sensing—were integrated to develop ratiometric pH responsive FFN probes. Through a systematic effort, Mini202 emerged as a promising probe, enabling in situ pH measurement of catecholamine secretory vesicles and methamphetamine-induced pH changes in PC-12 cells. Mini202 is sufficiently bright, photostable and suitable for two-photon microscopy. This new agent complements the fluorescent protein tags and enables the study of mechanisms controlling the secretory pathways in neuroendocrine cells and in neurotransmission. Also, screening of drugs and other agents for their effects on pH of secretory vesicles (e.g., transmitter releasing activity or toxicity screens) is possible. The pH measurement of individual presynaptic terminals in the brain is also feasible.

Example 8

Testing of Compound Mini110

Compound Mini110 is tested following the protocols described in Examples 4-6 and using procedures described in Example 7.

Compound Mini110 exhibits photophysical properties, pH responsiveness, and lipophilicity similar to Compound Mini102.

REFERENCES 1. (a) Chen, G.; Yee, D. J.; Gubernator, N. G.; Sames, D. *J. Am. Chem. Soc.* 2005, 127, 4544-4545. (b) Halim, M.; Tremblay, M. S.; Jockusch, S.; Turro, N. J.; Sames, D. *J. Am. Chem. Soc.* 2007, 129, 7704-7705. (c) Tremblay, M. S.; Halim, M.; Sames, D. *J. Am, Chem. Soc.* 2007, 129, 7570-7577. (d) Froemming, M. K.; Sames, D. *J. Am. Chem. Soc.* 2007, 129, 14518-14522. (e) Tremblay, M. S.; Lee, M.; Sames, D. *Org. Lett.* 2008, 10, 5-8. (f) Halim, M.; Yee, D. J.; Sames, D. *J. Am. Chem. Soc.* 2008, 130, 14123-14128.
2. (a) Sharma, V.; Wang, Q.; Lawrence, D. S. *Biochim. Biophys. Acta.* 2008, 1784, 94-99. (b) Lukovic, E.; Vogel Taylor, E.; Imperiali, B. *Angew. Chem. Int. Ed.* 2009, 48, 6828-6831.

Gubernator, N. G.; Zhang, H.; Stall, R. G. W.; Mosharov, E. V.; Pereira, D.; Yue, M.; Balsanek, V.; Vadola, P. A.; Mukherjee, B.; Edward, R. H.; Sulzer, D.; Sames, D. *Science* 2009, 324, 1441-1444.

4. Greene, L. A.; Tischler, A. S. *Proc. Natl. Acad. Sci. U.S.A.* 1976, 73, 2424-2428.

5. Yelin, R.; Schuldiner, S. *Neurotransmitter Transporters: Structure, Function, and Regulation.* 2nd. Ed., Totowa, N.J., Humana Press, 2002, 313-354.
6. (a) Miesenbock, G.; Angelis, D. A. D.; Rothman, J. E. *Nature* 1998, 394, 192-195. (b) Mani, M.; Ryan, T. A. *Front. Neural Circuits* 2009, 3, 1-9.
7. Wu, M. M.; Grabe, M.; Adams, S. l Tsien, R. Y.; Moore, H.-P. H.; Machen, T. E. *J. Biol. Chem.* 2001, 276, 33027-33035.
8. Haughland, R. P.; Spence, M. T. Z.; Johnson, I. D.; Basey, A. *The Hand book: A Guide to Fluorescent Probes and Labeling Technologies,* 10th ed., 2005, 937-955.
9. Markov, D.; Mosharov, E. V.; Setlik, W.; Gershon, M. D.; Sulzer, D. *J. Neurochem.* 2008, 107, 1709-1721.
10. Jones, R. C. F.; Bhalay, G.; Carter, P. A.; Duller, K. A. M.; Dunn, S. H. *J. Chem. Soc., Perkin Trans.* 1, 1999, 765-776.
11. Moreau, R. J.; Sorensen, E. J. *Tetrahedron* 2007, 63, 6446-6453.
12. Sun, W.-C.; Gee, K. R.; Haughland, R. P. *Bioorg. Med. Chem. Lett.* 1998, 8, 3107-3110.
13. Brun, M.-P.; Bischoff, L.; Garbay, C. Angew. *Chem. Int. Ed.* 2004, 43, 3432-3436.
14. (a) Llopis, J.; McCaffery, M.; Miyawaki, A.; Farquhar, M. G.; Tsien, R. Y. *Proc. Natl. Acad. Sci. U.S.A.* 1998, 95, 6803-6808. (b) Holopainen, F. M.; Saarikoski, J.; Kinnunen, P. K.; Jarvela, I. *Eur. J. Biochem.* 2001, 268, 5851-5856.
15. Sulzer, D.; Rayport, S. *Neuron* 1990, 5, 797-808.

What is claimed is:

1. A compound having the following structure:

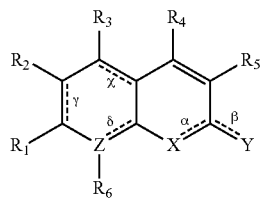

wherein
Y is O, X is O, bond α is absent and bond β is present;
atom Z is a carbon and bonds χ, δ and γ are present;
$R_1$ is —OH or —O⁻;
$R_2$ is —H, halogen, alkyl, alkenyl, alkynyl;
$R_3$ is —H, —OH, alkyl, alkenyl, alkynyl, or halogen; or $R_1$ is H, and $R_2$ together with $R_3$ form a substituted or unsubstituted aromatic ring;
$R_4$ is —CH$_2$CH$_2$NH$_2$, or —CH$_2$CH$_2$N(R$_8$)$_2$,
  wherein R$_8$ is alkyl, alkoxycarbonyl, alkenyl, or alkynyl; and
$R_5$ is —H, —CH$_2$CH$_2$NH$_2$, or —(C═O)CH$_2$CH$_2$NH$_2$, —CH$_2$CH$_2$N(R$_9$)$_2$,
  wherein R$_9$ is alkyl, alkoxycarbonyl, alkenyl, or alkynyl;
or
$R_4$ is —H, —CH$_2$CH$_2$NH$_2$, or —CH$_2$CH$_2$N(R$_8$)$_2$,
  wherein R$_8$ is alkyl, alkoxycarbonyl, alkenyl, or alkynyl; and
$R_5$ is —CH$_2$CH$_2$NH$_2$, or —(C═O)CH$_2$CH$_2$NH$_2$, —CH$_2$CH$_2$N(R$_9$)$_2$,
  wherein R$_9$ is C$_4$-C$_{12}$ alkyl, alkoxycarbonyl, alkenyl, or alkynyl; and
$R_6$ is H, alkyl, alkenyl, alkynyl, or halogen;

wherein each occurrence of alkyl, alkoxy, alkenyl, or alkynyl is substituted or unsubstituted, straight chain or branched, or a pharmaceutically acceptable salt thereof.

2. The compound of claim 1,
wherein $R_6$ is H, alkyl, alkenyl, or alkynyl,
or a pharmaceutically acceptable salt thereof.

3. The compound of claim 1,
wherein
$R_4$ is —H and $R_5$ is —CH$_2$CH$_2$NH$_2$;
$R_4$ is —CH$_2$CH$_2$NH$_2$ and $R_5$ is —H; or
$R_4$ is —CH$_2$CH$_2$NH$_2$ and $R_5$ is —CH$_2$CH$_2$NH$_2$,
or a pharmaceutically acceptable salt thereof.

4. The compound of claim 3, wherein $R_3$ is H or halogen.

5. The compound of claim 4 having the structure:

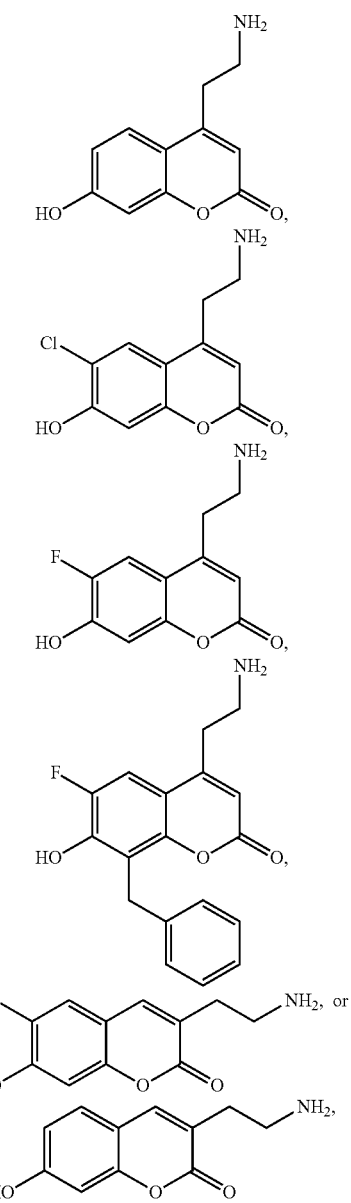

or a pharmaceutically acceptable salt thereof.

6. The compound of claim 5 having the structure:

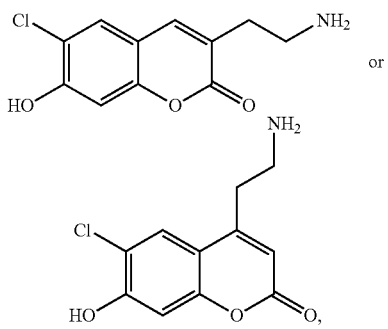

or a pharmaceutically acceptable salt thereof.

7. The compound of claim 4 having the structure:

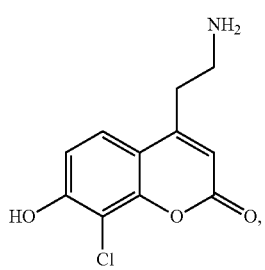 [SMILES: NCCc1cc(=O)oc2c(Cl)c(O)ccc12]

or a pharmaceutically acceptable salt thereof.

8. A process for preparing a compound having the structure

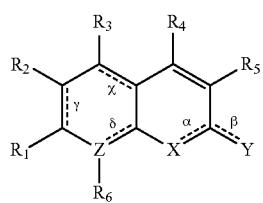

wherein
Y is O, X is O, bond α is absent and bond β is present;
atom Z is a carbon and bonds χ, δ and γ are present;
$R_1$ is —OH or —O⁻;
$R_2$ is —H, halogen, alkyl, alkenyl, alkynyl;
$R_3$ is —H, —OH, alkyl, alkenyl, alkynyl, or halogen;
or
$R_1$ is H, and $R_2$ together with $R_3$ form a substituted or unsubstituted aromatic ring;
$R_4$ is —CH$_2$CH$_2$NH$_2$, or —CH$_2$CH$_2$N(R$_8$)$_2$,
wherein $R_8$ is alkyl, alkoxycarbonyl, alkenyl, or alkynyl; and
$R_5$ is —H, —CH$_2$CH$_2$NH$_2$, or —(C═O)CH$_2$CH$_2$NH$_2$, —CH$_2$CH$_2$N(R$_9$)$_2$,
wherein $R_9$ is alkyl, alkoxycarbonyl, alkenyl, or alkynyl;
or
$R_4$ is —H, —CH$_2$CH$_2$NH$_2$, or —CH$_2$CH$_2$N(R$_8$)$_2$,
wherein $R_8$ is alkyl, alkoxycarbonyl, alkenyl, or alkynyl; and
$R_5$ is —CH$_2$CH$_2$NH$_2$, or —(C═O)CH$_2$CH$_2$NH$_2$, —CH$_2$CH$_2$N(R$_9$)$_2$,
wherein $R_9$ is C$_4$-C$_{12}$ alkyl, alkoxycarbonyl, alkenyl, or alkynyl; and $R_6$ is H, alkyl, alkenyl, alkynyl, or halogen;
wherein each occurrence of alkyl, alkoxy, alkenyl, or alkynyl is substituted or unsubstituted, straight chain or branched, comprising:
a) contacting a compound having the structure

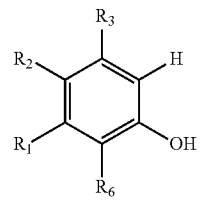

with a compound having the structure

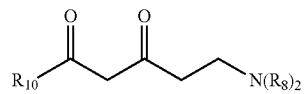

wherein $R_{10}$ is —OH, alkoxy, alkenyloxy, alkynyloxy, aryloxy, halogen, or heteroaryl,
wherein each occurrence of alkoxy, alkenyloxy, alkynyloxy, aryloxy, and heteroaryl is substituted or unsubstituted;
or
a') contacting a compound having the structure

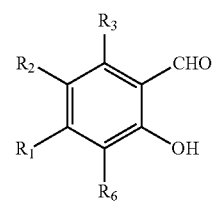

with a compound having the structure

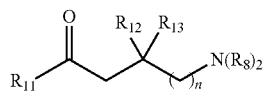

wherein $R_{11}$ is —OH, alkoxy, alkenyloxy, alkynyloxy, aryloxy, halogen, or heteroaryl;
$R_{12}$ and $R_{13}$ are each H or together form ═O;
n is 1 or 2;
wherein each occurrence of alkoxy, alkenyloxy, alkynyloxy, aryloxy, and heteroaryl is substituted or unsubstituted;
to form a compound having the structure

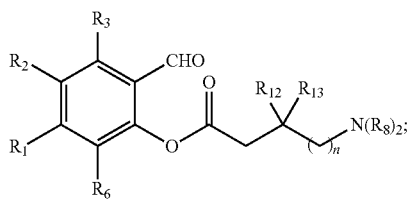

b') contacting the compound formed in step a') with a suitable base; so as to prepare the compound.

9. The process of claim 8,
wherein in the compound, $R_6$ is H, alkyl, alkenyl, or alkynyl.

10. The process of claim 8, comprising:
a) contacting a compound having the structure

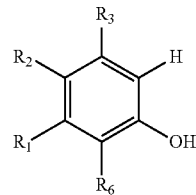

with a compound having the structure

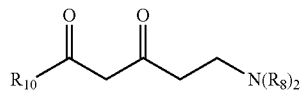

wherein $R_{10}$ is —OH, alkoxy, alkenyloxy, alkynyloxy, aryloxy, halogen, or heteroaryl,
wherein each occurrence of alkoxy, alkenyloxy, alkynyloxy, aryloxy, and heteroaryl is substituted or unsubstituted.

11. The process of claim 8, comprising:
a') contacting a compound having the structure

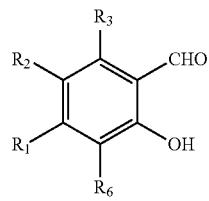

with a compound having the structure

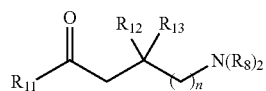

wherein $R_{11}$ is —OH, alkoxy, alkenyloxy, alkynyloxy, aryloxy, halogen, or heteroaryl;
$R_{12}$ and $R_{13}$ are each H or together form =O;
n is 1 or 2;
wherein each occurrence of alkoxy, alkenyloxy, alkynyloxy, aryloxy, and heteroaryl is substituted or unsubstituted;
to form a compound having the structure

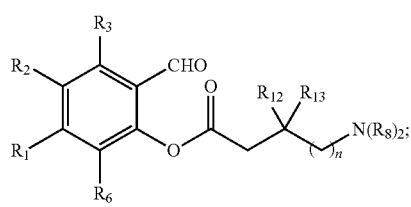

b') contacting the compound formed in step a') with a suitable base.

12. The process of claim 10, wherein the compound prepared has the structure:

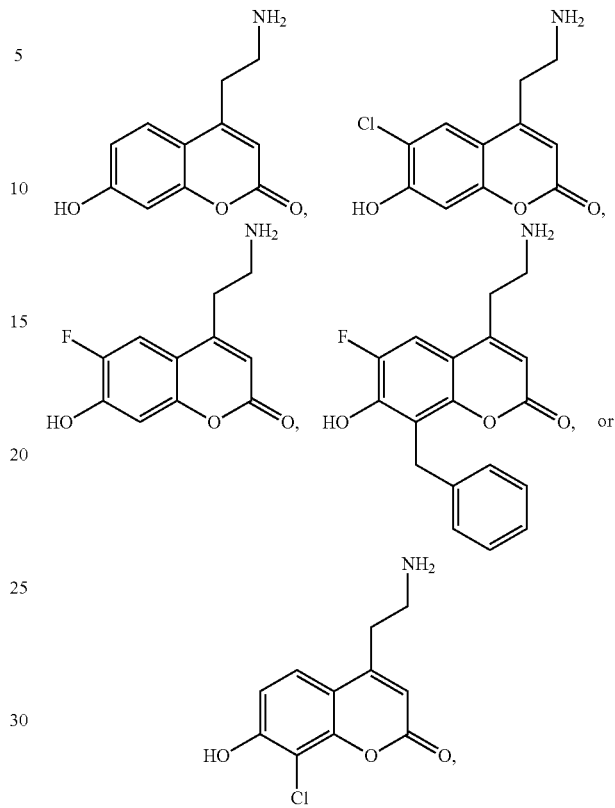

13. The process of claim 10, wherein the compound prepared has the structure:

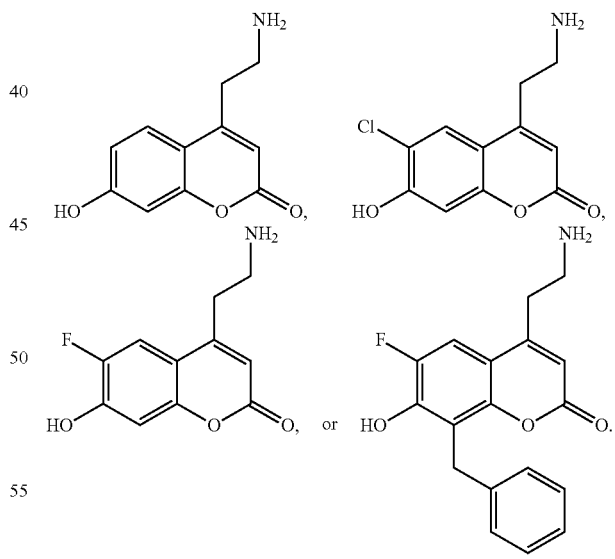

14. The process of claim 13, wherein the compound prepared has the structure:

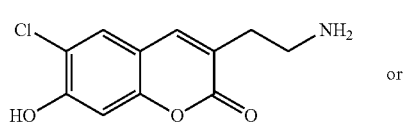

-continued
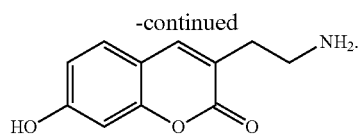
* * * * *